United States Patent
Todd et al.

(10) Patent No.: US 8,338,159 B2
(45) Date of Patent: Dec. 25, 2012

(54) CHICKEN VIRUS VACCINE AND DIAGNOSTIC

(75) Inventors: Daniel Todd, Belfast (GB); Brian Adair, Belfast (GB); Mildred Wylie, Belfast (GB); Neris Ball, Belfast (GB)

(73) Assignee: The Queen's University of Belfast, Belfast (GB)

( * ) Notice: Subject to any disclaimer, the term of this patent is extended or adjusted under 35 U.S.C. 154(b) by 202 days.

(21) Appl. No.: 12/087,477

(22) PCT Filed: Jan. 4, 2007

(86) PCT No.: PCT/GB2007/050005
§ 371 (c)(1),
(2), (4) Date: Dec. 8, 2008

(87) PCT Pub. No.: WO2007/077464
PCT Pub. Date: Jul. 12, 2007

(65) Prior Publication Data
US 2009/0092634 A1 Apr. 9, 2009

(30) Foreign Application Priority Data
Jan. 4, 2006 (GB) .................................. 0600081.4

(51) Int. Cl.
*C12N 7/01* (2006.01)
*A61K 39/21* (2006.01)
(52) U.S. Cl. .................................. 435/235.1; 536/23.72
(58) Field of Classification Search .................. None
See application file for complete search history.

(56) References Cited

U.S. PATENT DOCUMENTS 6,696,562 B1 * 2/2004 Schultz-Cherry et al. . 536/23.72
2005/0079485 A1 4/2005 Schultz-Cherry et al. ........ 435/5

FOREIGN PATENT DOCUMENTS

WO WO2004/027053 A1 * 4/2004

OTHER PUBLICATIONS

Jacobsen et al. Nucleic Acid Research, 2004, vol. 32, Nol. 7, pp. 1-10.*
Phillip McClean 1998, Nucleic Acid Hybridizations in DNA-Basic of Structure and Analysis, pp. 1-6.*
Koopmans et al. Clin Diagnostic Laboratory Immunology, 1998, vol. 5, No. 1 pp. 33-37.*
Jacobsen et al. Nucleic Acid Research, 2004, vol. 32, Nol. 7, pp, 1-10.*
Benkhadir, K. et al: "Molecular cloning and functional expression of the alpha-scorpion toxin BotIII: pivotal role of the C-terminal region for its interaction with voltage-dependent sodium channels", *PEPTIDES*, 25 151-161 (2004).
Koci, M. D. et al: "Avian astroviruses", *Avian Pathology*, 31 213-227 (2002).
Todd, D. et al: "Diagnosis of enterovirus-like viruses and astroviruses of chickens", *Irish Veterinary Journal*, 59(8) 436-436 (2006).
McNulty, M. S. et al: "Production and Preliminary Characterization of Monoclonal Antibodies to Chicken Anemia Agent", *Avian Diseases*, 34 352-358 (1990).

* cited by examiner

*Primary Examiner* — Bao Li
(74) *Attorney, Agent, or Firm* — Drinker Biddle & Reath LLP

(57) ABSTRACT

A novel astrovirus designated chicken astrovirus type 3 has been isolated and characterized. Nucleotide sequences and polypeptide sequences of this astrovirus are provided with uses of the same and the isolated astrovirus in assay kits and vaccines.

22 Claims, 3 Drawing Sheets

|  | ELV3(a) | ELV3(b) | CAstV-1 ANV | ELV1(a) | CAstV-2 | ELV4 | TAstV-1 | TAstV-2 |
|---|---|---|---|---|---|---|---|---|
| ELV3(a) | - | 98.5 | 47.7 | 47.7 | 84.6 | 83.8 | 58.8 | 70.8 |
| ELV3(b) |  | - | 48.5 | 48.5 | 84.6 | 85.4 | 58.0 | 70.0 |
| CAstV-1 ANV |  |  | - | 92.2 | 49.2 | 49.2 | 45.8 | 51.5 |
| ELV1(a) |  |  |  | - | 50.8 | 50.0 | 46.6 | 52.2 |
| CAstV-2 |  |  |  |  | - | 94.6 | 57.3 | 70.0 |
| ELV4 |  |  |  |  |  | - | 56.5 | 70.0 |
| TAstV-1 |  |  |  |  |  |  | - | 57.3 |
| TAstV-2 |  |  |  |  |  |  |  | - |

Figure 1

SEQUENCE LISTING

<160> NUMBER OF SEQ ID NOS: 9

<210> SEQ ID NO 1
<211> LENGTH: 391
<212> TYPE: DNA
<213> ORGANISM: Artificial
<220> FEATURE:
<223> OTHER INFORMATION: Sequence obtained from chicken astrovirus type 3

<400> SEQUENCE: 1

```
aaagcccttg ttttggcgca ttaggcagat tcggtttttt ttttttagcct caaagtataa      60 gacgcaggaa aacaaggagc tgtttgattg gtacaccaaa aaccttttgg agaaggtgat     120
attgttacct actggggaag tgtgccaaat aaagcgagga aatccttcag ggcaattttc     180
taccaccgtg gataacaaca tgtgcaacgt atggttaacc acctttgaaa tagcatggct     240
ccaccgcaaa caacggggca gactaccaac cccagctgaa ttgcgtgaaa acgtttgtta     300
tatttgctac ggtgatgaca ggctcttatc agtttcgaga gactttgtca tttatgagcc     360
tgaaactgtg gtagcaatgt acgcagatgt a                                    391
```

<210> SEQ ID NO 2
<211> LENGTH: 391
<212> TYPE: DNA
<213> ORGANISM: Artificial
<220> FEATURE:
<223> OTHER INFORMATION: sequence obtained from chicken astrovirus type 3

<400> SEQUENCE: 2

```
aaaacccttg ttttggcgca ttaggcagat tcggtttttc ttttttagcct caaagtataa      60 gacgcaggaa aacaaggagc tgtttgattg gtacaccaaa aaccttttgg agaaggtgat     120
attgttacct actggggaag tgtgccaaat aaagcgagga aatccttcag ggcaactttc     180
```

```
taccaccgtg gataacaaca tgtgcaacgt atggttaacc accttttgaaa tagcatggct    240 ccaccgcaaa caacggggca gactaccaac cccagctgaa ttgcgtgaaa acgtttgtta    300
tatttgctac ggtgatgaca ggcccttatc agtttcgaga actttgtca tttatgagcc     360 tgaaactgtg gtagcaatgt acgcagatgt a                                   391

<210> SEQ ID NO 3
<211> LENGTH: 391
<212> TYPE: DNA
<213> ORGANISM: Artificial
<220> FEATURE:
<223> OTHER INFORMATION: FP3 sequence

<400> SEQUENCE: 3
aaagcccttg ttttggcgta ttaggcagat tcggtttttc ttcttagcct caaagtataa    60
gacgcaggaa acaaggacc tctttgattg gtacaccaaa aacctcttgg agaaggtgat    120
attgttacct actggagaag tgtgccaaat aaagcgaggg aatccttcag ggcaattttc    180
tactaccgtg gataacaaca tgtgcaatgt atggctaacc accttttgaaa tagcatggct    240 tcaccgcaaa caacgggta gattaccaac cccagctgaa ttgcgtgaaa atgtttgtta    300
tatttgctac ggtgatgata ggctcttatc agtttcaaga actttgtca tttatgagcc     360 tgacactgtg gtagcgatgt acgctgatgt a                                   391

<210> SEQ ID NO 4
<211> LENGTH: 3265
<212> TYPE: DNA
<213> ORGANISM: Artificial
<220> FEATURE:
<223> OTHER INFORMATION: sequence obtained from chicken astrovirus type
      3

<400> SEQUENCE: 4
aaagcccttg ttttggcgca ttaggcagat tcggtttttt ttttagcct caaagtataa    60 gacgcaggaa acaaggagc tgtttgattg gtacaccaaa aacctttgg agaaggtgat    120 attgttacct actggggaag tgtgccaaat aaagcgagga atccttcag ggcaattttc    180 taccaccgtg gataacaaca tgtgcaacgt atggttaacc accttttgaaa tagcatggct    240 ccaccgcaaa caacggggca gactaccaac cccagctgaa ttgcgtgaaa acgtttgtta    300
tatttgctac ggtgatgaca ggctcttatc agtttcgaga actttgtct tttatgagcc     360 tgaaactgtg gtagcaatgt acgcagatgt attcggcatg tgggtgaagc cagagaatgt    420
gaaggtaaga aatacactta gtggtctctc tttctgtggt atgacaatta caaaaaatca    480
gcatggccgt tatgttggta ttcctaatgt caataaaata ctgtccactc tacggtctcc    540
tacaaagcgc cttccaaatg tagaagcact atggggtaag ttgatatcat taagaattct    600
gtgtgagaat gcagatcccg acgtaaagga ttacttagat aggcagatca attgcgtcga    660
ggagtatgcc gctgctgaag aaatacagtt accagaagtc gggcccgact tctttcagaa    720
aatctggtag agggatggac cgaaatatag cagcatggcc gataaggcta gcgcgcagaa    780
ggagaaaaca acaaggcgcg gacgtggccg ttctcgatct aggtcacgtt ctcgttcccg    840
ttctaggaat cgtgtcaaga aaactgtcac gatagttgaa tctaagaaaa ccccatctag    900
atctatatta agaaaagaac ttgaaaatca tgagagaagg gataggaggc gttttaggaa    960
gattgaaaaa aaattaaatg gccctaaaat acatgatcgc atggcagtca caactacact    1020
tggagtcctc actggaaatt ctgacaataa tttggaaagg aaaatgagag ctcttcttaa    1080
```

```
cccattgctt ttgaaatctc aaaacactgg ggcctcagca tccccacttt cccttagggc    1140
atctcagtat tcaatgtgga agatacagaa atgtgttgta aaatttgttc ccctagttgg    1200
ggctgctaat gtggcaggta gtgtatcctt tgtgtctctg gatcaggatg caacctcctc    1260
ccagcctgaa tcacctgata cgataaaggc aaggtgcat gcagaagttg caattggaca     1320
aagatttaat tggaacgttc aatctagata cctggtcgga ccccgttctg gttggtgggg    1380
catggatact ggtgagtcac caactgatac agttggacca gcccttgact tttgaatct     1440
ttatagaaca gtgaacacac ttcaaactgg ctcaacatcg caggcataca ctgcaccatt    1500
gttttctatt gaagtgtata cggtgtatgt tttttcaggt tacgaaccaa agcctgccct    1560
ggcgaccatg acaaattcaa cttttgagag tcagcagggg gtgaccataa caaatggtgc    1620
taatggtgaa cttctgctca atgttccacg gcgatcgagt cttgccgaag gctgcgtga    1680
aaaggaagta ttataccgcg gccaaaacca acgggtggt gtcggtgagg tactgtgggc     1740
ggtggcatca ggagctgttg aaggagctgc agaagcgttg ggcccatggg gatggttact    1800
gagaggtggc tggtgggtga taaagaagtt gtttggacgg agcgctgaaa atgaaagtga    1860
cgattatgtg atgtactcgt ctattgagga tgccaacaaa gatagtagga tctatcaaac    1920
ggtatccagt gcggtccctg ttcaacaagg tcctctggtt ctcacccaaa tctcatcccc    1980
aaatgttaat caagctgggg gtgttgtgca ggtaggtaca acaattgcca ctgattactt    2040
gccactatct caggcccagg ttccgctttt agagaacatt ctttactcca gcactgggca    2100
gcctgtgaca tcaactaaga gccatactat gaggatcact gggtttccag cctcgaaatt    2160
ggtaacatca acgtcgtcgc aatggttggg cactactgat acgagtgtcc aagcaacaaa    2220
gtggctaatg tcggattata cagacactgg agtgatattt ggcttttccat actctgatga   2280
ttccccccggg gaaacttttg gtaacattgg agtaatacac acagccaagt cgctcataaa   2340
aacggtcaca tcaaggcgac aacgcgggct acgcatgtct ccacttgttt cgacattgtt    2400
accatcaact tctaagggac caacccagat gcttagttgc tttgacacgc cttactattg    2460
gattagggtt tgtgacaata cctgctcaaa caaacccaca aatggcgccg tgacacagcg    2520
ctgcaatgct tggggcgtta tggtggtgag cttagcacac aataaagtct acatcttggc    2580
tggttatccc gattctcaaa ctagggtacc acaacaacaa ctagtctggg cacttttga    2640
ctgggatgct acatttttcta ctggcaggat ttataataca acatggccag gactttatga   2700
agaaagtgat gatgaaacag atgccgaatc tgacatctcc agtcttttg accccgttaa     2760
tgaggttgag caggactttc acttcaaatg tagtctgaag acatctgact acttgaagga    2820
ggaggctgat tattggaaag caaaagcaca acaattgctt atggagaaag caatgggaaa    2880
aaataatgac tctcctccac ttgtccgctt tgagaagggc ggacctgagc agcaaaaaca    2940
gcctgctagc agccgcggcc acgccgagta ggatcgaggg tacagctgca ccttcttcat    3000
ggagttttta tgccataatc aggcttttct ccatgtaaat caaggcaccg ggccacgcc    3060
gagcaggaac gagggtacag tgccgggttg accccacctg aaagggggcgt ccgccggtgt   3120
gataatcacc acaccggggc ctggtttaaa tcacagataa tcactctgtg tgtcaatcag    3180
gtctttcggg cggttttgga aacactagtt tttaaaacca atttgatttt gaattagatt    3240
aattggcaaa aaaaaaaaaa aaaaa                                          3265
```

<210> SEQ ID NO 5
<211> LENGTH: 738
<212> TYPE: PRT
<213> ORGANISM: Artificial
<220> FEATURE:

-continued

<223> OTHER INFORMATION: Protein encoded by chicken astrovirus type 3

<400> SEQUENCE: 5

```
Met Ala Asp Lys Ala Ser Ala Gln Lys Glu Lys Thr Thr Arg Arg Gly
1               5                   10                  15

Arg Gly Arg Ser Arg Ser Arg Ser Arg Ser Arg Ser Arg Asn
            20                  25                  30

Arg Val Lys Lys Thr Val Thr Ile Val Glu Ser Lys Lys Thr Pro Ser
            35                  40                  45

Arg Ser Ile Leu Arg Lys Glu Leu Glu Asn His Glu Arg Arg Asp Arg
        50                  55                  60

Arg Arg Phe Arg Lys Ile Glu Lys Lys Leu Asn Gly Pro Lys Ile His
65                  70                  75                  80

Asp Arg Met Ala Val Thr Thr Thr Leu Gly Val Leu Thr Gly Asn Ser
                85                  90                  95

Asp Asn Asn Leu Glu Arg Lys Met Arg Ala Leu Leu Asn Pro Leu Leu
            100                 105                 110

Leu Lys Ser Gln Asn Thr Gly Ala Ser Ala Ser Pro Leu Ser Leu Arg
        115                 120                 125

Ala Ser Gln Tyr Ser Met Trp Lys Ile Gln Lys Cys Val Val Lys Phe
    130                 135                 140

Val Pro Leu Val Gly Ala Ala Asn Val Ala Gly Ser Val Ser Phe Val
145                 150                 155                 160

Ser Leu Asp Gln Asp Ala Thr Ser Ser Gln Pro Glu Ser Pro Asp Thr
                165                 170                 175

Ile Lys Ala Lys Val His Ala Glu Val Ala Ile Gly Gln Arg Phe Asn
            180                 185                 190

Trp Asn Val Gln Ser Arg Tyr Leu Val Gly Pro Arg Ser Gly Trp Trp
        195                 200                 205

Gly Met Asp Thr Gly Glu Ser Pro Thr Asp Thr Val Gly Pro Ala Leu
    210                 215                 220

Asp Phe Trp Asn Leu Tyr Arg Thr Val Asn Thr Leu Gln Thr Gly Ser
225                 230                 235                 240

Thr Ser Gln Ala Tyr Thr Ala Pro Leu Phe Ser Ile Glu Val Tyr Thr
                245                 250                 255

Val Tyr Val Phe Ser Gly Tyr Glu Pro Lys Pro Ala Leu Ala Thr Met
            260                 265                 270

Thr Asn Ser Thr Phe Glu Ser Gln Gln Gly Val Thr Ile Thr Asn Gly
        275                 280                 285

Ala Asn Gly Glu Leu Leu Asn Val Pro Arg Arg Ser Ser Leu Ala
    290                 295                 300

Glu Gly Leu Arg Glu Lys Glu Val Leu Tyr Arg Gly Gln Asn Gln Thr
305                 310                 315                 320

Gly Gly Val Gly Glu Val Leu Trp Ala Val Ala Ser Gly Ala Val Glu
                325                 330                 335

Gly Ala Ala Glu Ala Leu Gly Pro Trp Gly Trp Leu Leu Arg Gly Gly
            340                 345                 350

Trp Trp Val Ile Lys Lys Leu Phe Gly Arg Ser Ala Glu Asn Glu Ser
        355                 360                 365

Asp Asp Tyr Val Met Tyr Ser Ser Ile Glu Asp Ala Asn Lys Asp Ser
    370                 375                 380

Arg Ile Tyr Gln Thr Val Ser Ser Ala Val Pro Val Gln Gln Gly Pro
385                 390                 395                 400

Leu Val Leu Thr Gln Ile Ser Ser Pro Asn Val Asn Gln Ala Gly Gly
```

405                 410                 415
Val Val Gln Val Gly Thr Thr Ile Ala Thr Asp Tyr Leu Pro Leu Ser
                420                 425                 430

Gln Ala Gln Val Pro Leu Leu Glu Asn Ile Leu Tyr Ser Ser Thr Gly
            435                 440                 445

Gln Pro Val Thr Ser Thr Lys Ser His Thr Met Arg Ile Thr Gly Phe
        450                 455                 460

Pro Ala Ser Lys Leu Val Thr Ser Thr Ser Gln Trp Leu Gly Thr
465                 470                 475                 480

Thr Asp Thr Ser Val Gln Ala Thr Lys Trp Leu Met Ser Asp Tyr Thr
                485                 490                 495

Asp Thr Gly Val Ile Phe Gly Phe Pro Tyr Ser Asp Ser Pro Gly
            500                 505                 510

Glu Thr Phe Gly Asn Ile Gly Val Ile His Thr Ala Lys Ser Leu Ile
        515                 520                 525

Lys Thr Val Thr Ser Arg Arg Gln Arg Gly Leu Arg Met Ser Pro Leu
    530                 535                 540

Val Ser Thr Leu Leu Pro Ser Thr Ser Lys Gly Pro Thr Gln Met Leu
545                 550                 555                 560

Ser Cys Phe Asp Thr Pro Tyr Tyr Trp Ile Arg Val Cys Asp Asn Thr
                565                 570                 575

Cys Ser Asn Lys Pro Thr Asn Gly Ala Val Thr Gln Arg Cys Asn Ala
            580                 585                 590

Trp Gly Val Met Val Val Ser Leu Ala His Asn Lys Val Tyr Ile Leu
        595                 600                 605

Ala Gly Tyr Pro Asp Ser Gln Thr Arg Val Pro Gln Gln Leu Val
610                 615                 620

Trp Asp Thr Phe Asp Trp Asp Ala Thr Phe Ser Thr Gly Arg Ile Tyr
625                 630                 635                 640

Asn Thr Thr Trp Pro Gly Leu Tyr Glu Glu Ser Asp Asp Glu Thr Asp
                645                 650                 655

Ala Glu Ser Asp Ile Ser Ser Leu Phe Asp Pro Val Asn Glu Val Glu
            660                 665                 670

Gln Asp Phe His Phe Lys Cys Ser Leu Lys Thr Ser Asp Tyr Leu Lys
        675                 680                 685

Glu Glu Ala Asp Tyr Trp Lys Ala Lys Ala Gln Leu Leu Met Glu
            690                 695                 700

Lys Ala Met Gly Lys Asn Asn Asp Ser Pro Pro Leu Val Arg Phe Glu
705                 710                 715                 720

Lys Gly Gly Pro Glu Gln Gln Lys Gln Pro Ala Ser Ser Arg Gly His
                725                 730                 735

Ala Glu

<210> SEQ ID NO 6
<211> LENGTH: 22
<212> TYPE: DNA
<213> ORGANISM: Artificial
<220> FEATURE:
<223> OTHER INFORMATION: Forward primer

<400> SEQUENCE: 6
agcctcaaag tataagacgc ag                                          22

<210> SEQ ID NO 7
<211> LENGTH: 22
<212> TYPE: DNA

<213> ORGANISM: Artificial
<220> FEATURE:
<223> OTHER INFORMATION: Reverse primer

<400> SEQUENCE: 7
ccatgctatt tcaaaggtgg tt                                          22

<210> SEQ ID NO 8
<211> LENGTH: 29
<212> TYPE: DNA
<213> ORGANISM: Artificial
<220> FEATURE:
<223> OTHER INFORMATION: AstPol-1F
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: modified base
<220> FEATURE:
<221> NAME/KEY: misc_feature
<222> LOCATION: (12)..(12)
<223> OTHER INFORMATION: modified base
<220> FEATURE:
<221> NAME/KEY: modified_base
<222> LOCATION: (12)..(12)
<223> OTHER INFORMATION: I
<220> FEATURE:
<221> NAME/KEY: misc_feature
<222> LOCATION: (21)..(21)
<223> OTHER INFORMATION: modified base
<220> FEATURE:
<221> NAME/KEY: modified_base
<222> LOCATION: (21)..(21)
<223> OTHER INFORMATION: I
<220> FEATURE:
<221> NAME/KEY: misc_feature
<222> LOCATION: (24)..(24)
<223> OTHER INFORMATION: modified base
<220> FEATURE:
<221> NAME/KEY: modified_base
<222> LOCATION: (24)..(24)
<223> OTHER INFORMATION: I
<220> FEATURE:
<221> NAME/KEY: misc_feature
<222> LOCATION: (27)..(27)
<223> OTHER INFORMATION: modified base
<220> FEATURE:
<221> NAME/KEY: modified_base
<222> LOCATION: (27)..(27)
<223> OTHER INFORMATION: I

<400> SEQUENCE: 8
gaytggacnm gntaygaygg nacnatncc                                   29

<210> SEQ ID NO 9
<211> LENGTH: 18
<212> TYPE: DNA
<213> ORGANISM: Artificial
<220> FEATURE:
<223> OTHER INFORMATION: AstPol-1R
<220> FEATURE:
<221> NAME/KEY: modified_base
<222> LOCATION: (4)..(4)
<220> FEATURE:
<221> NAME/KEY: misc_feature
<222> LOCATION: (4)..(4)
<223> OTHER INFORMATION: modified base
<220> FEATURE:
<221> NAME/KEY: modified_base
<222> LOCATION: (13)..(13)
<220> FEATURE:
<221> NAME/KEY: misc_feature
<222> LOCATION: (13)..(13)

```
<223> OTHER INFORMATION: modified base

<400> SEQUENCE: 9
yttnacccac atnccraa                                                    18
```

CHICKEN VIRUS VACCINE AND DIAGNOSTIC

FIELD OF THE INVENTION

The present invention relates to vaccines, assay kits and detection methods for a novel astrovirus, in particular chicken astrovirus type 3 (CAstV-3). Infections of broiler chickens with this chicken astrovirus type 3 are associated with enteritis and growth depression and possible adverse effects on chick embryo development.

BACKGROUND

Growth depression problems in young chickens, known in the poultry production industry by various terms such as "stunting", "runting-stunting" or "uneven growth" syndrome, result in considerable economic costs for affected farms. Such growth depression has been associated with infections with a variety of viruses including rotaviruses and as yet uncharacterised, small round viruses, known as enterovirus like viruses (ELV). Since the clinical problems caused by specific viruses are ill-defined due to the lack of specific diagnostic tests, it is difficult to accurately estimate the demand for a vaccine to protect against virus-induced growth depression problems.

Virus infections of chickens can be horizontally transmitted from virus that may be contaminating the chicken house; for example, with enteric infections, fecal-oral spread is likely to be common. It is also recognised that vertical transmission of enteric infections via the embryo from virus-infected parent chickens may also occur.

Previous studies (Veterinary Laboratories Agency (VLA), Weybridge), have shown that an enterovirus like virus (ELV), designated FP3, could be detected in the meconium (gut contents) of dead-in-shell chicks, suggesting that this ELV was infecting the embryo and was vertically transmitted from infected parents [Spackman et al. 1984].

Enterovirus-like viruses include picornaviruses, astroviruses, caliciviruses and the like and small non-enveloped spherical viruses which replicate in the cytoplasm. They have an RNA genome and are stable at pH3. Several ELVs which are antigenically distinct from each other have been suggested to cause growth depression in avians.

SUMMARY OF INVENTION

Following extensive virological investigation of sick birds from UK flocks in 2004-5, the present inventors have successfully isolated an infectious agent from weak chicks. Characterisation of this agent suggests that this viral agent causes growth depression in young chickens and possible adverse effects on chick embryos.

According to a first aspect of the present invention there is provided an isolated novel astrovirus strain designated, CAstV-3. A sample of this strain has been deposited under Accession number CNCM I-3541 at CNCM, Institut Pasteur on 15 Dec. 2005.

Astroviruses are small spherical viruses which typically have 5 or 6 pointed star morphology and a positive sense single strand RNA genome of around 7 kb.

A number of astroviruses have been previously characterised in duck, turkeys and chickens, however, the astrovirus characterised by the present inventors is antigenically distinct as demonstrated by indirect immunofluorescence assays.

A substantial region (~3.3 kb) of the genome of CAstV-3 has been sequenced. This region comprises part of the astrovirus ORF1 b, the astrovirus RNA dependent RNA polymerase, a small intergenic sequence of 24 nucleotides, and astrovirus ORF 2, which encodes the capsid protein region, and the 3' untranslated region.

According to a second aspect, the present invention provides an isolated nucleotide sequence which has at least 85%, preferably at least 90%, preferably at least 93%, more preferably at least 95%, more preferably at least 98%, even more preferably at least 99%, and most preferably 100% sequence identity to
  (a) a nucleotide sequence as set out in any one of SEQ ID NOs 1 to 4,
  (b) a nucleotide sequence that is capable of hybridising to any one of SEQ ID NOs 1 to 4 under stringent conditions, or
  (c) a fragment of (a) or (b).

Suitably a nucleotide sequence of the invention encodes an amino acid sequence which is capable of generating an immunogenic response against chicken astrovirus type 3. Suitably a fragment of a nucleotide sequence of (a) or (b) encodes an amino acid sequence which is capable of generating an immunogenic response against chicken astrovirus type 3.

Suitably the immunogenic response is against at least one antigenic site provided by a capsid protein of chicken astrovirus type 3 (CAstV-3).

The invention further provides a gene construct including at least one nucleotide sequence of the second aspect of the invention and a control sequence, for example a promoter.

There is further provided a vector including an isolated nucleotide sequence according to the second aspect of the invention and a promoter which is operably linked to said nucleotide sequence. Suitable vectors include viruses (eg. Vaccinia virus, adenovirus, baculovirus etc), yeast vectors, phage, chromosomes, artificial chromosomes, plasmids or cosmid DNA.

According to a third aspect of the invention there is provided a method of producing a polypeptide encoded by a nucleotide sequence of the invention, or fragment thereof, including the steps of:
  (a) contacting a bacterial cell and/or an insect cell via a baculovirus and/or a yeast cell and/or a plant cell with a vector as described herein, and
  (b) cultivating said bacterial cell and/or an insect cell and/or a yeast cell and/or a plant cell under conditions suitable for the production of polypeptide or fragment thereof.

Suitably the bacterial cell may be *Escherichia coli*.

Suitably the polypeptide is encoded by a nucleotide sequence of any one of SEQ ID NOs 1 to 4.

Suitably the polypeptide is encoded by a nucleotide sequence of chicken astrovirus type 3.

The invention further provides a polypeptide produced substantially from the above method. As will be understood by those of skill in the art such a polypeptide may be isolated or substantially purified from the mixture in which it is expressed.

According to a fourth aspect of the present invention there is provided a polypeptide sequence encoded by any nucleotide sequence of the second aspect of the invention.

Preferably there is provided a polypeptide sequence encoded by any one of SEQ ID Nos 1 to 4.

Suitably a polypeptide of the invention may be antigenic in that it exhibits at least one antigenic site to which an immune response can be directed.

Antigenic polypeptides derived from CAstV-3, for example a capsid protein (SEQ ID NO 5) or fragments thereof, are within the scope of the present invention.

Suitably there is provided a polypeptide which has at least at least 85%, preferably at least 90%, preferably at least 93%, more preferably at least 95%, more preferably at least 98%, even more preferably at least 99%, and most preferably 100% sequence identity to a polypeptide with amino acids as set out in SEQ ID NO: 5.

Polyclonal and monoclonal antibodies which specifically bind to a polypeptide of the present invention are also within the scope of the invention as are the use of said antibodies. As will be understood by those of skill in the art such antibodies may be isolated or substantially purified from the mixture in which they are provided.

According to a fifth aspect of the invention there is provided
 (i) the use of an isolated novel astrovirus strain designated, CAstV-3 of the first aspect of the invention,
 (ii) the use of a nucleotide sequence of the second aspect of the invention, or
 (iii) the use of a polypeptide of the fourth aspect of the invention in the preparation of a composition which is capable of mediating an immune response in an avian.

According to a sixth aspect of the invention there is provided a composition prepared according to the fifth aspect of the invention.

Suitably said composition includes at least part of the isolated novel astrovirus of the first aspect of the invention, at least one nucleotide sequence of the second aspect of the invention, or at least one polypeptide of the fourth aspect of the invention.

Vaccination, the induction of adaptive immunity, of broiler chickens is advantageous as vaccination can be used to control clinical disease. Chicks produced from vaccinated parents are likely to be less susceptible to adverse clinical effects caused by the infectious agent vaccinated against during the early growing period of the broiler chicken.

Accordingly a seventh aspect of the present invention provides a vaccine for immunisation against growth depression in an avian wherein said vaccine comprises a composition according to the sixth aspect for inducing an immune response in avians.

The present invention also provides a method of vaccinating avians against CAstV-3 by providing an immunologically effective amount of said vaccine.

Isolated CAstV-3 and/or nucleotides of the invention and/or polypeptides and/or antibodies provided by the invention may be used for the preparation of a diagnostic assay of the invention. Such assays can be used to detect avian astrovirus in samples, for example tissues, feces and serum from avians suspected of being infected with the virus.

According to an eighth aspect of the present invention there is provided a diagnostic assay for the detection of chicken astrovirus type 3 in samples from avians suspected of being infected with the virus comprising the steps:
 (i) contacting avian physiological material with a probe wherein said probe is selected from:
  (a) a nucleotide sequence as set out in any one of SEQ ID NOs 1 to 4,
  (b) a nucleotide sequence that is capable of hybridising to any one of SEQ ID NOs 1 to 4 under stringent conditions,
  (c) a nucleotide sequence which has at least 85%, preferably at least 90%, preferably at least 93%, more preferably at least 95%, more preferably at least 98%, even more preferably at least 99% and most preferably 100% sequence identity to a nucleotide sequence as set out in any one of (a) to (b),
  (d) a fragment of (a) (b) or (c),
  (e) a polypeptide encoded by a nucleotide sequence as set out in any one (a) to (d), or
  (f) an antibody with binding specificity to a polypeptide of (e), and
 (ii) detecting a successful binding event between the probe and at least one component of the sample.

Suitably said probe may be selected from
 (a) a nucleotide sequence as set out in any one of SEQ ID NOs 1 to 4,
 (b) a nucleotide sequence that is capable of hybridising to any one of SEQ ID NOs 1 to 4 under stringent conditions,
 (c) a fragment of (a) or (b),
 (d) a polypeptide thereof encoded by a nucleotide sequence as set out in any one (a) to (c), or
 e) an antibody with binding specificity to a polypeptide of (d).

In a particular embodiment a probe may be a suitable primer set for use in RT-PCR to amplify a selected target sequence of chicken astrovirus type 3.

Suitably the fragment encodes a polypeptide capable of generating an antigenic response similar to that provided by a polypeptide encoded by any one of nucleotide sequences SEQ ID NO 1 to 4.

Suitably the binding event is detected using a marker associated with the probe, for example a fluorescent marker, a radioisotope marker or the like.

In one embodiment the assay comprises the steps:
 (i) contacting avian physiological material, for example blood, containing antibodies which specifically bind to at least part of chicken astrovirus type 3, with at least part of chicken astrovirus type 3, wherein said at least part of chicken astrovirus type 3 has preferably been immobilized on a solid surface, such that said antibodies are capable of binding to the at least part of chicken astrovirus type 3, and
 (ii) detecting the presence of said bound antibodies.

In a further embodiment a diagnostic assay method may comprise the steps;
 (i) contacting a sample of avian physiological material, for example feces containing avian astrovirus type 3, with an antibody which specifically binds to at least part of chicken astrovirus type 3, which antibody has preferably been immobilised on a solid substrate, such that said antibody is capable of binding to said avian astrovirus type 3, and
 (ii) detecting the presence of said bound virus The captured virus may be detected through the use of antibody with specificity to the virus in conjugated form as would be known to those of skill in the art.

In a further embodiment a diagnostic assay method may comprise the steps;
 (i) providing genetic material from avian physiological material, and
 (ii) testing the genetic material to detect any genetic material from chicken astrovirus type 3.

Suitably a probe may be a nucleic acid sequence capable of binding to a nucleotide sequence of the invention, preferably a nucleotide sequence of chicken astrovirus type 3, preferably a nucleotide sequence of any one of SEQ ID NOs: 1 to 4.

Suitably a probe may be a primer set capable of binding to a nucleotide sequence of chicken astrovirus type 3, preferably a nucleotide sequence of any one of SEQ ID NOs: 1 to 4, to allow amplification of a sequence via RT-PCR.

According to a further aspect of the present invention there is provided a diagnostic kit for use in the diagnosis of chicken astrovirus type 3 (CAstV-3), which includes a probe wherein said probe is at least one of (a) a sequence as set out in any one of SEQ ID NOs 1 to 4,
(b) a sequence that is capable of hybridising to any one of SEQ ID NOs 1 to 4 under stringent conditions,
(c) a nucleotide sequence which has at least 85%, preferably at least 90%, preferably at least 93%, more preferably at least 95%, more preferably at least 98%, even more preferably at least 99% and most preferably 100% sequence identity to a nucleotide sequence as set out in any one of (a) or (b),
(d) a fragment of (a), (b) or (c),
(e) a polypeptide thereof encoded by a nucleotide sequence as set out in any one (a) to (d), or
(f) an antibody with binding specificity to a polypeptide of (e).

Suitably the fragment encodes a polypeptide capable of generating an antigenic response similar to that provided by a polypeptide encoded by any one of nucleotide sequences SEQ ID NO 1 to 4.

Suitably the probe is associated with a marker, for example a fluorescent marker, a radioisotope marker or the like.

DETAILED DESCRIPTION

Virus

The invention relates to isolated chicken astrovirus type 3 and characterisation of the nucleotide sequences and polypeptide of said virus.

Pairwise amino acid identity comparison by the inventors of CAstV-3 with other avian astroviruses suggests that the closest homology it shares with known astroviruses is with CAstV-2. The pairwise amino acid identity between CAstV-3 and CAstV-2 is 84.6%.

In relation to nucleotide sequences provided by the invention, sequence identity is determined using a suitable mathematical algorithm. Computer implementations of such mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version8 (available from Genetics Computer Group (GCG), 575 Science Drive, Madison, Wis., USA).

Suitably alignments using these programs may be performed using the default parameters.

As used herein, "sequence identity" or "identity" in the context of two nucleotide or polypeptide sequences makes reference to a specified percentage of residues in the two sequences that are the same when aligned for maximum correspondence over a specified comparison window, as measured by sequence comparison algorithms or by visual inspection.

Suitably, a specified comparison window is selected from a sequence encoding or representing at least 50, at least 100, at least 150, at least 200, at least 250, or most preferably all of the amino acids of a specified polypeptide being aligned.

When percentage of sequence identity is used in reference to proteins it will be understood by those of skill in the art that residue positions which are not identical often differ by conservative amino acid substitutions, i.e. wherein amino acids are substituted with amino acids which have similar chemical properties to those amino acids which are replaced. The percent sequence identity may be adjusted upwards to correct for the conservative nature of a substitution.

Hybridisation refers to the binding, duplexing, or hybridizing of a molecule only to a particular nucleotide sequence under stringent conditions when that sequence is present in a complex mixture (e.g., total cellular) DNA or RNA.

Stringent hybridisation occurs when a nucleic acid binds the target nucleic acid with minimal background. Typically, to achieve stringent hybridisation, temperatures of around 1° C. to about 20° C., more preferably 5° C. to about 20° C. below the Tm (melting temperature at which half the molecules dissociate from their partner) are used. However, it is further defined by ionic strength and pH of the solution.

An example of highly stringent wash conditions is 0.15 M NaCI at 72° C. for about 15 minutes. An example of a stringent wash condition is a 0.2×SSC wash at 65° C. for 15 minutes (see, Sambrook and Russell, infra, for a description of SSC buffer). Often, a high stringency wash is preceded by a low stringency wash to remove background probe signal. An example of a medium stringency wash for a duplex of, for example, more than 100 nucleotides, is 1×SSC at 45° C. for 15 minutes. An example of a low stringency wash for a duplex of for example more than 100 nucleotides, is 4-6×SSC at 40° C. for 15 minutes. For short probes (for example about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30-G ° C. and at least about 60° C. for long probes (for example, >50 nucleotides).

Suitably nucleotide sequences of the present invention encode antigenic polypeptides of chicken astrovirus type 3.

Suitably the present invention provides an isolated nucleotide sequence selected from (a) a nucleotide sequence as set out in any one of SEQ ID NOs 1 to 4,
(b) a nucleotide sequence that is capable of hybridising to any one of SEQ ID NOs 1 to 4 under stringent conditions,
(c) or a fragment of (a) or (b).

In specific embodiments nucleotide sequences of the invention consist of any one of nucleotide sequences selected from SEQ ID NO 1, 2, 3 and/or 4.

Suitably, the nucleotide sequences of the present invention may be expressed to provide the encoded polypeptides.

Preferably polypeptides of the present invention include polypeptides encoded by a nucleotide sequence selected from (a) a nucleotide sequence as set out in any one of SEQ ID NOs 1 to 4,
(b) a nucleotide sequence that is capable of hybridising to any one of SEQ ID NOs 1 to 4 under stringent conditions,
(c) or a fragment of (a) or (b).

Polypeptide fragments of the present invention may be a variant of any one of the polypeptides encoded by any one of SEQ ID NOs: 1 to 4 which include one or more truncations, substitutions, deletions or insertions wherein said polypeptides provide an antigenic response similar to that of any one of the polypeptides encoded by SEQ ID NOs: 1 to 4. Advantageously these variations may be made to the protein to enhance the efficacy of the protein in stimulating immune response or to make it safer for use in an avian.

The length of such a fragment which provides an immune response comprises at least 6, up to 15, preferably 25, and more preferably 50 contiguous amino acids encoded by any one of SEQ ID No 1 to SEQ ID No 4. An antigenic fragment may be generated using, for example, C terminal deletion of any one of the polynucleotide sequences of SEQ ID No 1 to SEQ ID No 4 and said C terminal deletion constructs may then be inserted into suitable prokaryotic or eukaryotic expression plasmid. The antigenic activity of the expression products derived from the polynucleotide fragments may then be tested by assessing reactivity with antisera from naturally and/or experimentally infected chickens using immunoblotting methods.

Alternatively a series of overlapping synthetic peptides specified by the sequence of the CAstV-3 proteins, preferably the capsid protein could be generated. These peptides may then be reacted with antisera from naturally or experimentally infected chickens using an ELISA method to determine which peptides are antigenic. Additionally, synthetic peptides may be used to immunise mice, rabbits, chickens and the antisera produced can be assessed for reactivity with CAstV-3 using indirect immunofluorescence assays. In this way immunogenic peptides may be identified and virus-specific antisera can be elicited. These two latter approaches described are particularly advantageous for small peptides that contain linear, continuous epitopes.

Suitably the invention provides a polypeptide of amino acid sequence wherein between 1 to 5, 1 to 10, 1 to 15, or 1 to 20 amino acid residues are deleted, substituted, and/or added to the amino acid sequence encoded by the nucleotide sequences of any one of SEQ ID NOs:1 to 4 and wherein said polypeptides stimulate an immune response (i.e. have antigenic activity).

In specific embodiments nucleotide sequences of the invention encode a polypeptide of the following (a) or (b):
(a) a polypeptide comprising of an amino acid sequence of a SEQ ID NO: 5
(b) a protein comprising of an amino acid sequence when one or several amino acid residues are deleted, substituted, and/or added to the amino acid sequence of SEQ ID NO:5 wherein said protein has a similar antigenic response as SEQ ID NO:5.

In particular embodiments nucleotide sequences of the invention encode a polypeptide of the following (a) or (b):
(a) a polypeptide consisting of an amino acid sequence of a SEQ ID NO: 5
(b) a protein consisting of an amino acid sequence when one or several amino acid residues are deleted, substituted, and/or added to the amino acid sequence of SEQ ID NO 5 wherein said protein has a similar antigenic response as SEQ ID NO:5.

Nucleotide sequences may be codon-optimised or otherwise modified to increase the efficiency of expression of the polypeptides.

Suitably the invention provides polypeptides consisting of an amino acid sequence SEQ ID NO 5.

Polyclonal antibody sera may be produced through the use of at least part of CAstV-3 to raise an immune response. The immunising preparation could be purified virus from cell culture, virus-specified synthetic peptides, polypeptides produced by expression vectors etc; DNA expression plasmids. After repeated challenge, portions of the blood serum can be removed and antigenically purified. The semi-purified sera may additionally be purified using chromatography, for example, a saccharide gel column and suitable buffer to separate the components of the sera according to molecular weight.

Suitably the invention provides polyclonal antibodies which have binding specificity to at least one polypeptide of the invention.

Suitably the invention provides polyclonal antibodies which have binding specificity to
(a) at least one polypeptide sequence encoded by a nucleotide sequence of any one of SEQ ID Nos 1 to 4,
(b) at least one polypeptide sequence comprising of an amino acid sequence when one or several amino acid residues are deleted, substituted, and/or added to the amino acid sequence encoded by any one of SEQ ID Nos 1 to 4 wherein said polypeptide has a similar antigenic response as a polypeptide encoded by any of nucleotide sequences SEQ ID NO: 1 to 4, or
(c) a fragment of the polypeptide of (a), (b) which has a similar antigenic response as a polypeptide encoded by any of nucleotide sequences SEQ ID NO: 1 to 4.

Suitably the invention provides polyclonal antibodies which have binding specificity to
(a) at least one polypeptide sequence encoded by a nucleotide sequence of any one of SEQ ID Nos 1 and/or 2 and/or 4,
(b) at least one polypeptide comprising of an amino acid sequence when one or several amino acid residues are deleted, substituted, and/or added to the amino acid sequence encoded by any one of SEQ ID Nos 1 and/or 2 and/or 4 wherein said polypeptide has a similar antigenic response as a polypeptide encoded by any of nucleotide sequences SEQ ID NO: 1 and/or 2 and/or 4, or
(c) a fragment of the polypeptide of (a), (b) which has a similar antigenic response as a polypeptide encoded by any of nucleotide sequences SEQ ID NO: 1, 2 or 4.

Suitably such a polyclonal antibody does not have binding specificity to polypeptides encoded by SEQ ID NO: 3

Preferably the invention provides polyclonal antibodies which have binding specificity to (a), (b), or (c) wherein
(a) is at least one polypeptide with amino acid sequence SEQ ID NO 5,
(b) is at least one polypeptide comprising of an amino acid sequence when one or several amino acid residues are deleted, substituted, and/or added to the amino acid sequence of SEQ ID NO 5 wherein said polypeptide has a similar antigenic response as SEQ ID NO 5
(c) is a fragment of the polypeptide of (a), (b) or (c) which has a similar antigenic response as SEQ ID NO 5.

Monoclonal antibodies may be produced by the hybridoma technique, for example, immunisation of a mouse may be used to generate mouse monoclonal antibodies Suitably the invention provides a monoclonal antibody which has binding specificity to at least one polypeptide of the invention.

Suitably the invention provides a monoclonal antibody which has binding specificity to
(a) at least one polypeptide sequence encoded by a nucleotide sequence of any one of SEQ ID Nos 1 to 4,
(b) at least one polypeptide comprising of an amino acid sequence when one or several amino acid residues are deleted, substituted, and/or added to the amino acid sequence encoded by any one of SEQ ID Nos 1 to 4 wherein said protein has a similar antigenic response as a polypeptide encoded by any of nucleotide sequences SEQ ID NO: 1 to 4, or
(c) a fragment of the polypeptide of (a), (b) which has a similar antigenic response as a polypeptide encoded by any of nucleotide sequences SEQ ID NO: 1 to 4.

Suitably the invention provides a monoclonal antibody which has binding specificity to (a) at least one polypeptide sequence encoded by a nucleotide sequence of any one of SEQ ID Nos 1 and/or 2 and/or 4, (b) at least one polypeptide comprising of an amino acid sequence when one or several amino acid residues are deleted, substituted, and/or added to the amino acid sequence encoded by any one of SEQ ID Nos 1 and/or 2 and/or 4 wherein said polypeptide has a similar antigenic response as a polypeptide encoded by any of nucleotide sequences SEQ ID NO: 1 and/or 2 and/or 4, or (c) a fragment of the polypeptide of (a), (b) which has a similar antigenic response as a polypeptide encoded by any of nucleotide sequences SEQ ID NO: 1, 2 or 4.

Suitably such a monoclonal antibody does not have binding specificity to polypeptides encoded by SEQ ID NO: 3

Preferably the invention provides a monoclonal antibody which has binding specificity to (a), (b), or (c) wherein
- (a) is a polypeptide with amino acid sequence SEQ ID NO 5,
- (b) is at least one polypeptide comprising of an amino acid sequence when one or several amino acid residues are deleted, substituted, and/or added to the amino acid sequence of SEQ ID NO 5 wherein said protein has a similar antigenic response as SEQ ID NO 5, or
- (c) is a fragment of the polypeptide of (a), (b) or (c) has a similar antigenic response as SEQ ID NO 5.

Immunisation to provide monoclonal antibodies may be performed, for example as detailed below or may involve a combination of more than one of these three methods.

1) CAstV-3 may be purified from embryo-grown virus or virus present in infected avian feces, for example chicken feces, and used for immunisation.

2) Mice may be immunised with recombinant chicken astrovirus type 3, for example CAstV-3, protein produced by expression of chicken astrovirus type 3 polynucleotide sequence (preferably a polynucleotide sequence encoding a capsid protein) in *E. coli*, yeast, plant or insect cells infected with a recombinant baculovirus.

3) Mice may be immunised with a DNA expression plasmid capable of expressing avian astrovirus type 3 polynucleotide sequence, for example a polynucleotide sequence of CAstV-3 including at least one of SEQ ID NO 1 to 4.

As indicated above, these preparations can also be used to produce polyclonal antibodies.

The presence of antibodies to avian astrovirus type 3, for example CAstV-3 in the immunised mice can be detected using an indirect immunofluorescence (IIF) test.

Hybridoma cells can be prepared from the spleens removed from the immunised mice and cloned cell cultures can be screened for their abilities to secrete virus-specific antibodies using an IIF test.

Antibodies produced in an animal treated with a protein of the present invention can be isolated and used as an assay and/or for assay purposes.

In particular the invention provides the use of an antibody which has binding specificity to polypeptides encoded by any one of SEQ ID No 1 to 4 in a diagnostic assay.

As will be appreciated by those in the art an "antibody" should be construed as covering any binding member or substance having a binding domain with the required specificity. An antibody may be natural or partly or wholly synthetically produced. The term also covers any polypeptide, protein or peptide having a binding domain that is, or is homologous to, an antibody binding domain. These can be derived from natural sources, or they may be partly or wholly synthetically produced. Examples of antibodies are the immunoglobulin isotypes and their isotopic subclasses and fragments which comprise an antigen binding domain such as Fab, scFv, Fv, dAb, Fd, and diabodies.

An avian may be a chicken, turkey, duck, quail, goose, ostrich, pheasant, peafowl, guinea fowl, pigeon, swan, bantam and/or penguin.

Treatment

A virus, nucleic acid sequence, protein or antibody of the invention may be used to modify the immune system of an avian. Such modulation may be used to treat an avian.

Treatment includes any regimen that can benefit an avian. The treatment may be in respect of an existing condition or may be prophylactic (preventative treatment). Treatment may include curative, alleviation or prophylactic effects.

Treatment may be provided via any suitable route. The precise dose will depend upon a number of factors, for example the precise nature of the antigen of the vaccine or the use of particular adjuvants.

Vaccine or Composition to Mediate an Immune Response

A vaccine or composition to mediate an immune response of the present invention can comprise live virus, live attenuated virus or inactivated CAstV-3. Suitably, a vaccine of the present invention may comprise immunogenic derivatives and/or at least part of CAstV-3, including, for example, antigenic subunits, vectors able to express nucleotide sequences of the invention, including CAstV-3 nucleotide sequences, SEQ ID NO 1 to 4, for example a DNA vaccine encoding a polypeptide of the invention, for example a capsid protein of CAstV-3 (SEQ ID NO 5), recombinant chicken astrovirus type 3, synthetic peptide vaccines, or the like.

Suitably to inactivate the virus a standard chemical inactivating agent, such as aldehyde reagent including formalin, acetaldehyde and the like may be used. Alternatively, irradiation (for example, ultraviolet or Gamma irradiation) of the virus may be used or the virus may be repeatedly grown in cell culture from non-avian origin such that its ability to virulently reproduce is lost.

A vaccine of the present invention may be used in avians for immunisation against growth depression.

Derivatives of polypeptides of the present invention may be used to mediate immune response. Polypeptides of the invention may be suitably linked to a coupling partner, e.g. an effecter molecule, a label, a drug, a toxin and/or a carrier or transport molecule. Techniques for coupling the polypeptides of the invention to both peptidyl and non-peptidyl coupling partners are well known in the art.

Suitably the vaccine may comprise a pharmaceutical carrier or diluent, for example physiological saline, propylene glycol and the like.

Suitably the vaccine may comprise an adjuvant, for example, Freund's incomplete adjuvant.

Method of Vaccination

The vaccine may be delivered orally, parenterally, intranasally or intravenously. The dosage of the vaccine provided will typically take into account the age and/or weight and/or physical condition of the avian.

Suitably the vaccine may be provided in drinking water, spray or as an aerosol, for mass vaccination of poultry such as, but not limited to, chickens and turkeys.

In one embodiment a vaccine may be prepared as a live vaccine, which will be administered via drinking water or by a spray. Such a vaccine may be non-attenuated, since it is likely that infections of the growing breeder birds (say 10 weeks and older) will not result in pathogenic effects. (Infections of very young chicks (e.g. 0-3 weeks) are likely to be pathogenic.)

In a second embodiment a vaccine may be prepared as an attenuated virus which may be produced by growing the virus in embryos or cell culture. Such an attenuated vaccine could also be given by drinking water or spray. It is also possible that an attenuated or non-attenuated CAstV-3 virus could be given by inoculation (e.g. subcutaneous route).

In a third embodiment a vaccine may be prepared as a dead or inactivated virus. Inactivated (dead) virus may be administered by inoculation. The adjuvant used with inactivated virus will likely be important in order to maximise the immune response elicited.

In a fourth embodiment a vaccine may be prepared as a recombinant subunit vaccine. This approach may be adopted, for example, if live vaccines are not efficacious and if inactivated vaccines are too expensive to produce. A recombinant subunit vaccine may be based on expression of capsid protein in *E. coli*, yeast, plant or insect cells infected by a recombinant baculovirus. In such an embodiment at least part of CAstV-3 may be used to prepare the vaccine, for example a protein (preferably a structural protein) of CAstV-3 may be used. Such a protein may be produced by recombinant DNA expression methodologies or by culturing the virus.

Suitably the vaccine to avian astrovirus type 3, for example CAstV-3 may further comprise antigens of other agents, for example other avian, more specifically other chicken viruses, as part of a combination vaccine.

Assay Method

In particular embodiments, an assay of the invention comprises the steps:
- providing a sample from an avian,
- bringing into contact with the sample an antibody capable of binding specifically to at least part of chicken astrovirus type 3 (CAstV-3),
- detecting binding of the antibody to CAstV-3 in the sample wherein the binding of the antibody to chicken astrovirus type 3 in the sample is indicative of the presence of CAstV-3, in the avian.

Suitably the antibody capable of binding specifically to chicken astrovirus type 3 is capable of binding a polypeptide encoded by SEQ ID NOs 1 to 4, more preferably a polypeptide encoded by SEQ ID NOs 1, 2 or 4, more preferably a polypeptide with an amino acid sequence SEQ ID NO 5 or at least part of the polypeptide of SEQ ID NO 5 which is antigenic.

In alternative embodiments, an assay of the invention comprises the steps:
- bringing into contact with the sample at least part of chicken astrovirus type 3,
- detecting the presence or absence of binding of at least part of chicken astrovirus type 3 to an antibody in the sample wherein the binding of the at least part of the isolated chicken astrovirus type 3 to an antibody is indicative of the presence of antibodies to chicken astrovirus type 3 in the avian.

In further alternative embodiments, an assay of the invention comprises the steps:
(i) providing genetic material, and
(ii) testing the genetic material to detect any genetic material from chicken astrovirus type 3.

Suitably the genetic material is from an avian and may be RNA from an avian, for example a chicken.

Suitably the genetic material may be taken from feathers, eggs, blood, feces, intestines, and intestinal contents, tissue or the like from an avian.

A number of commercial kits are available to extract RNA from tissue samples. These are well known to those skilled in the art.

The skilled person will be aware of a range of detection method for detecting genetic material in samples.

Suitably the method involves the use of a reverse transcription PCR (RT-PCR) reaction. In a particularly preferred embodiment the detection method comprises the steps
(i) providing forward and reverse primers for a nucleic acid polymerase, which primers are capable of binding specifically to a chicken astrovirus type 3 polynucleotide sequence;
(ii) amplifying polynucleotide sequence between the primers;
(iii) detecting amplified polynucleotide sequence;
wherein detection of multiple copies of amplified polynucleotide sequence in the sample is indicative of the presence of chicken astrovirus type 3 in the sample.

The basis of this test is that a positive cDNA product will be produced if the two small primer sequences find exact or very close sequence matches in the RNA extracted from the test samples.

Forward and reverse primers for a nucleic acid polymerase suitable for use in the invention may be selected from any suitable sequences from within the CAstV-3 genome. The skilled person would appreciate the factors required to be taken into account when designing suitable primers for example, the use of sequence comparisons to determine conserved regions of sequence to which forward and reverse primers may be designed.

Suitably the primers may have the sequence

```
Forward:
5'- AGC CTC AAA GTA TAA GAC GCA G-3'. SEQ ID No 6

Reverse:
5'- CCA TGC TAT TTC AAA GGT GGT T-3'. SEQ ID NO 7
```

Advantageously using such primers a test between 10, preferably 20, more preferably 30 and most preferably 100-fold more sensitive than a method using detection by indirect immunofluorescence of virus antigen produced by inoculating primary chick embryo liver cells with virus-containing samples is provided.

Preferably, the assay method provides quantitative information on the amount of virus present in the sample.

Advantageously the primers may be labelled fluorescently and the assay comprises the further step of determining if the primers have bound to the polynucleotide sequence by determining the fluorescent emissions of the primer.

Suitably fluorescent labels are within the common general knowledge of skilled persons.

Preferably the assay method of the invention is specific for chicken astrovirus type 3 as deposited under Accession number CNCM I-3541 at CNCM, Institut Pasteur on 15 Dec. 2005.

Any suitable sample may be used in an assay of the present invention, for example, a sample from an avian, for example a chicken may be used and a tissue where the virus replicates, for example, gut may be used. Alternatively, the sample may be blood or feces.

Preferably a sample for diagnosis may be selected from feces, gut contents or fecal swab.

Suitably when the sample is feces and/or gut contents, crude virus suspensions are prepared as 10% homogenates in phosphate buffered saline (PBS). These may be clarified using 3000 g for 30 minutes and an aliquot (eg 200 microlitre) of clarified extract is extracted. With swabs, suspensions in 1-2 ml PBS may be made and clarified as above prior to extraction.

Diagnostic Kit

In particular examples of diagnostic assay kits provided by the invention for the detection of chicken astrovirus type 3 in samples from avians suspected of being infected with the virus, the assay kit comprises at least part of chicken astrovirus type 3, a nucleotide sequence of the invention, a polypeptide of the invention, a polyclonal antibody of the invention or a monoclonal antibody of the invention.

The at least part of the chicken astrovirus type 3, nucleotide sequence of the invention, polypeptide of the invention, polyclonal antibody of the invention or monoclonal antibody of the invention may be bound to a substrate such that a test sample may be placed on or washed over the at least part of the chicken astrovirus type 3, nucleotide sequence of the invention, polypeptide of the invention, polyclonal antibody of the invention or monoclonal antibody of the invention.

In specific examples, a diagnostic assay kit of the invention for the detection of chicken astrovirus type 3 in samples from avians suspected of being infected with the virus comprises antibodies with binding specificity to at least part of chicken astrovirus type 3. Suitably, the antibodies may be bound to a substrate such that a test sample may be placed on or washed over the bound antibodies.

Suitably the antibodies have binding specificity to polypeptides encoded by any one of SEQ ID NOs: 1 to 4. In a particular embodiment the antibodies have a binding specificity to a polypeptide with an amino acid sequence SEQ ID NO: 5.

In a further example, a diagnostic assay kit of the invention for the detection of chicken astrovirus type 3 in samples from avians suspected of being infected with the virus comprises a nucleic acid probe capable of hybridising to any one of SEQ ID NOs 1 to 4.

In particular examples a nucleic acid probe capable of hybridising to any one of SEQ ID NOs 1, 2 or 4 is provided.

In one embodiment, a probe may be a nucleic acid sequence and the hybridisation of said probe to a nucleotide sequence in the sample may be detected by dot blot hybridisation.

Suitably the probe may be a primer set.

When a primer set is used, said primer set may be used amplify a selected sequence via RT-PCR if a particular nucleotide sequence is present in a sample.

In particularly preferred examples a primer set may be selected from:

```
Forward:
5'- AGC CTC AAA GTA TAA GAC GCA G-3'.  SEQ ID No 6

Reverse:
5'- CCA TGC TAT TTC AAA GGT GGT T-3'.  SEQ ID NO 7
```

Preferably the assay kit is specific for chicken astrovirus type 3 as deposited under Accession number CNCM 1-3541 at CNCM, Institut Pasteur on 15 Dec. 2005.

Suitably the virus, nucleotide sequences, polypeptide sequences, modulators of the immune system, vaccines and kits of the present invention may be used in relation to avians, more preferably any birds which are produced commercially, more preferably poultry such as chickens, turkeys, ducks, geese, pheasants, pigeons, guinea fowl, yet more preferably chickens.

DEFINITIONS

As used herein, the term "isolated" refers to an in vitro preparation, isolation and/or purification of a peptide, polypeptide, protein, antibody, virus or nucleic acid molecule of the invention, such that it is not associated with in vivo substances or is substantially purified from in vivo substances.

As used herein the term "aerosol" includes finely divided solid or liquid particles that may be created using a pressurised system such as a nebuliser.

As used herein the terms "nucleic acid" or "nucleotide sequence" includes genomic DNA, cDNA or RNA.

The invention described herein will now be exemplified with reference to the following non-limiting examples and figures. Other embodiments of this invention will be apparent to those of ordinary skill in the art in view of this description.

FIG. 1 shows pairwise amino acid identity comparison of ELVs and avian astroviruses;

INFECTION OF YOUNG CHICKENS WITH CASTV-3

Figure 2:
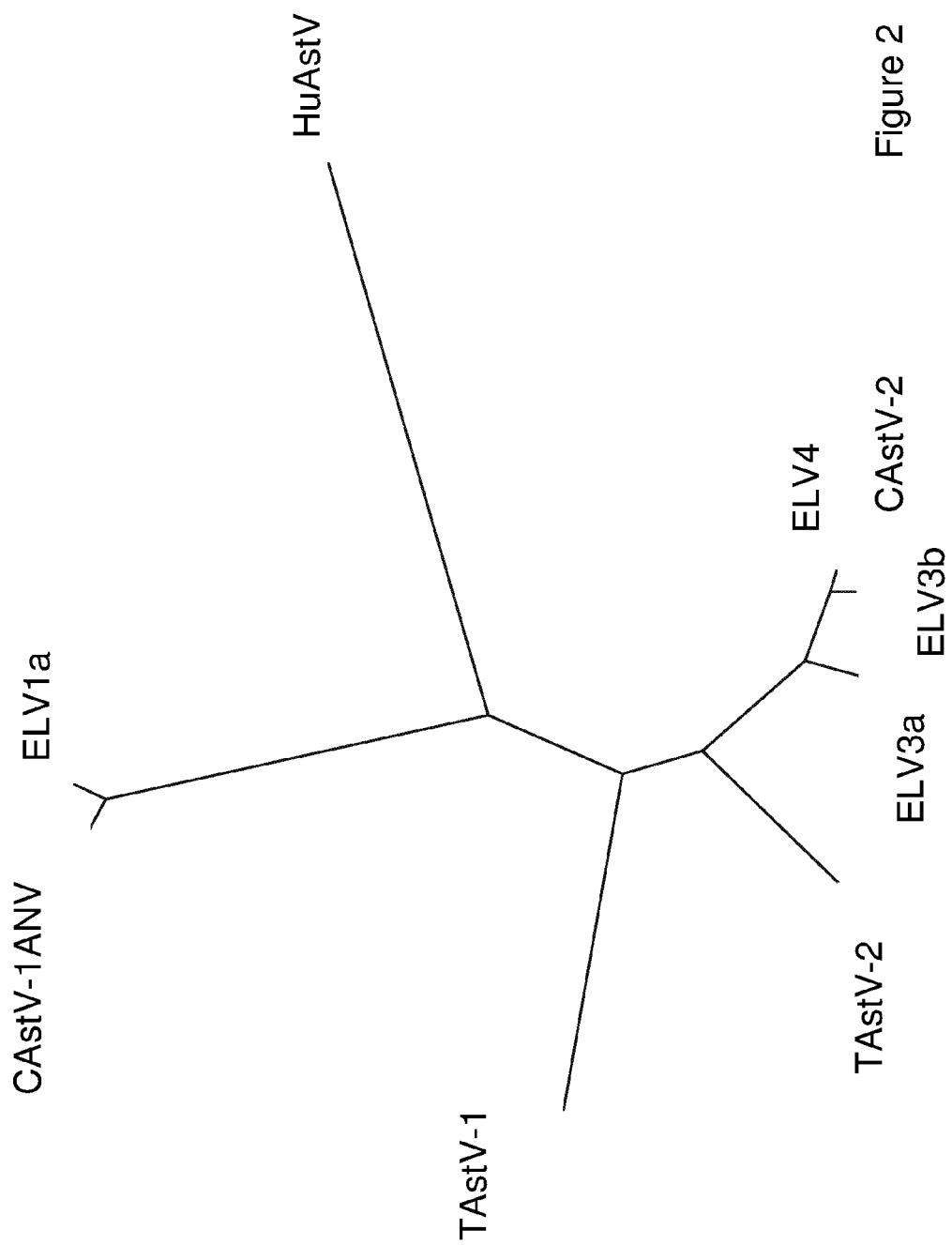
FIG. 2 shows phylogenetic analysis of Human, chicken and turkey astrovirus sequences.

Experimental and preliminary field investigations suggest that infections with the CastV-3 are associated with growth retardation or growth depression in young chickens.

Growth depression is a characteristic of disease states including stunting in which young birds fail to grow at the expected rate. This can be transient lasting days after which the affected birds will grow normally and "catch up" with their non-affected hatchmates. Alternatively, the birds may remain relatively small ("runting") and lag behind their non-affected hatchmates. Thus, the flock as a whole might be described as displaying "uneven growth".

Experimentally, it has been shown that oral inoculation of 1-day-old specific pathogen free (SPF) chickens with chicken astrovirus 3 resulted in a 17% depression in growth over a 14-day period. Histological changes were observed in the intestine, kidney and pancreas indicating that this virus replicated in the intestine but additionally had the ability to spread beyond the intestinal tract. Virus antigen was detected in a wide range of tissues. It is suggested that the observed growth depression may have been due to the combined effects on both the intestine and the other organs e.g. pancreas.

Evidence from the field involved investigation of clinical samples from flocks exhibiting "uneven growth", which showed that the gut contents from some clinically affected chickens contain large numbers of enterovirus-like viruses (ELV), including CAstV-3, together with rotaviruses and retroviruses. It is recognised that chicken astrovirus type 3 may be contributing to the clinical problem. In addition, oral infection of 1-day-old SPF chickens with an inoculum prepared from the gut contents from a sick chicken from a flock exhibiting uneven growth resulted in approximately 30% growth depression at 5 weeks post infection. Serological testing showed that the inoculated chickens had seroconverted to CAstV-3 and another immunologically distinct ELV identified previously. This finding indicated that the inoculum contained CAstV-3 and suggested that this virus may have been contributing to the growth retardation.

It is probable that the pathogenic effects caused by infections with enteric viruses such as CAstV-3 will be more severe in younger chickens and in chickens without maternal antibodies to the infecting viruses. It is recognised that the presence of maternal antibody may not prevent infections of the chicken intestinal tract due to the absence of antibody at this site, but may prevent or reduce the spread of the infection beyond the intestine.

Infection of Embryo with CAstV-3

Evidence for embryo transmission of CAstV-3 was observed in recent work by the inventors, which has demonstrated the presence of virus in gut tissues prepared from 1-day-old chicks obtained from several breeder flocks. Serological testing showed that the majority of breeder flocks displayed partial seroconversion to chicken astrovirus type 3 when tested at 22 weeks (just before they come into lay). Taken together these results support the view that many breeder birds become infected during lay and, that, as a consequence, are capable of transmitting CAstV-3 to their embryos and progeny chicks.

Inoculation of 6 or 7-day-old embryos with isolates of CAstV-3 including FP3, caused embryo death, dwarfing and liver and skin necrosis in embryos and reduced hatchability. Therefore, in the field infections with CAstV-3 have the potential to damage the developing embryo and to cause reduced hatchability.

Irrespective of whether CAstV-3 causes disease problems for the embryo, it is likely that vertically-transmitted virus will pose a threat to the newly-hatched chick, particularly since these chicks will not have maternally-derived antibody to the virus. Virus replication may cause pathogenic effects to these directly infected chicks. Virus excreted by these birds, often in the first few days, will in turn horizontally infect hatchmates that will either have maternal antibody (if the egg was produced by a previously-infected, antibody-positive breeder), or not have maternal antibody (if the egg was produced from an uninfected, antibody-negative breeder). The protective effect of maternal antibody is likely to lead to variation in the pathogenic effects observed and uneven growth within the broiler flock may be observed.

Isolation and Preliminary Characterization of the Infectious Agent

Using the chick embryo inoculation method, a number of successful attempts were made to isolate infectious agents from weak 1-day-old chickens from flocks displaying reduced hatchability and higher proportions of weak chicks. The following is one such example:

Weak chicks from sample submission "11672" were homogenised as whole chicks and inoculated into 7-day-old embryos via the yolk sac. No embryo deaths were recorded after 10 days of incubation, but the embryos were smaller than the controls. Samples of allantoic fluid from the eggs were processed and examined by EM, but no virus particles were seen. The livers from these embryos were pooled, homogenised and re-inoculated by the yolk sac route (1st pass) into 7-day-old eggs. With these samples, embryo deaths were recorded between 9 and 12 days after inoculation. The embryos were dwarfed, compared to the controls, and white lesions (areas of necrosis) were seen around the margins of the liver lobes. In these eggs, the allantoic fluid had a distinct green colour, and this was collected and stored (−70° C.). EM examination failed to reveal any evidence of virus particles.

Livers were removed from the dead embryos, pooled, homogenised and examined by electron microscopy but no virus particles were seen. The pooled liver was re-inoculated into 7-day-old eggs (2nd pass), and all embryos died with deaths recorded from day 4 post inoculation. The embryos were dwarfed and as before the allantoic fluid was a distinct green colour. Livers and kidneys were removed from the dead embryos and cryostat sections cut. The liver sections were stained by immunofluorescence for infectious bronchitis virus, but no positive fluorescence was observed. Liver and kidney cryostat sections were retained for staining with additional antisera at a later date. White necrotic lesions were seen on the livers from one set of samples, and some of this material was processed for thin section EM, but no evidence of virus replication was seen. Livers with necrotic lesions were homogenised and given 2×7 day passes in primary chick embryo liver cells. No viral CPE was observed, but the coverslips were fixed and stored at −20° C. to await fluorescent staining when a conjugate becomes available.

The 2nd pass material was subjected to additional passaging in chick embryos as outlined below. The pooled liver homogenate was again inoculated by yolk sac, this time into 7-day-old SPF embryos (3rd pass). Embryo deaths were recorded from day 7 to 11 post inoculation, and embryos were stunted with gross necrotic lesions on the liver and skin. Samples of affected liver were fixed and stored for histopathological examination and the remaining livers from the dead embryos were pooled together and homogenised. Allantoic fluids were collected separately and also pooled. The allantoic fluid was inoculated (4th pass) by yolk sac inoculation into 7-day-old embryos, resulting in embryo deaths between 7 and 10 days post inoculation. Allantoic fluids and livers were pooled and used to infect 7-day-old SPF embryos (5th pass). The embryos were collected, homogenised and stored at −70° C. This homogenate is referred to herein as the 11672 virus 1st pass Embryo Homogenate (1p EH).

Concentration and purification studies were undertaken with the homogenates derived from passaging the 11672 samples in embryos.

The homogenate of whole embryos was prepared after inoculating embryos with 11672 (1p EH), in an attempt to identify the agent responsible for the embryo mortality. Twelve 7-day-old VALO SPF eggs were inoculated and dwarfed embryos and green AF harvested after 7 days incubation. Different starting materials were used for purification. These were allantoic fluid, yolk stalks, green livers and whole embryos. A similar purification was used in each case. This involved 3 steps: (1) Clarification at 3000 rpm for 20 min, (2) Low-speed ultracentrifugation at 10000 rpm for 30 min, (3) High-speed ultracentrifugation at 30000 rpm for 3-4 hr. Centrifugations at 10,000 rpm and 30,000 rpm were performed in a Beckman ultracentrifuge (Type 35 fixed angle rotor).

With the liver and whole embryo preparations, an additional step was used. This involved resuspending the high-speed pellet, treatment or non-treatment of the suspension with the detergent sodium dodecyl sulphate (SDS) and sedimentation through 25% sucrose cushions using a 6×14 ml swing-out Beckman rotor centrifuged at 32000 rpm for 3-4 hr. This step was included because the high-speed pellets were thick and gelatinous and likely to contain high levels of embryo-derived contamination that would make the visualisation of virus particles very difficult. All samples of material obtained from the above preparations were negative by negative contrast EM and by immune EM using convalescent antiserum.

To better define if the infectivity was concentrated at one or more stages of the purification process, an homogenate of stunted whole embryos, from the 1p EH passage material was treated using steps 1, 2 and 3 above, with material being collected after each centrifugation step for inoculation into 7-day-old SPF embryos. All preparations produced dwarfing or death during 7 days incubation, indicating that the infectivity was present at all stages of the purification process, including the high-speed pellet. This result indicated that some infectious virus remained in association with cellular material in that infectivity was pelleted by the 10000 rpm centrifugation step (Table 1). Some infectious virus remained in the soluble 10000 rpm supernate fraction and was pelleted at 30000 rpm centrifugation. The detection of some infectivity in the 30000 rpm supernate suggested that 11672 virus may be small. However, using embryo inoculation to show virus infectivity in this way is a relatively crude method. Without titrating virus infectivity it is difficult to assess what proportions of infectivity were present in each fraction.

TABLE 1

Pattern of embryo deaths following inoculation of fractions from differential centrifugation.

| Treatment | Days post inoculation | | | | | | | Findings with embryos alive at day 12 |
|---|---|---|---|---|---|---|---|---|
| | 3 | 4 | 5 | 6 | 7 | 10 | 11 | |
| 10000 rpm supernates | | 1 | 1 | 1 | 2 | 5 | | 0 |
| 10000 rpm pellet (1:60) | | | 2 | 1 | 2 | 3 | | 2 very small (1 with liver necrosis) |
| 30000 rpm supernate | | | | | 1 | 2 | 1 | 3 small embryos 2 liver necrosis 2 liver enlarged |
| 30000 rpm pellet (1:60) | 1 | | 1 | 1 | | 4 | 1 | 2 normal |

10 eggs were inoculated with each fraction.

Pellet fractions were diluted 1:60 to account for concentration effect

Embryos remaining alive at day 12 p.i. were killed and examined.

To determine if the infectious agent was chloroform sensitive i.e. if the viral agent was enveloped (sensitive to chloroform treatment) or non-enveloped (resistant to chloroform), the 11672 virus embryo homogenate (2p EH) was treated with chloroform, then inoculated into 7-day-old embryos. Embryo death and stunting was recorded in both the treated and untreated preparations, indicating that the infectious agent was not enveloped.

The 11672 virus embryo homogenate (2p EH) was diluted from $10^{-1}$ to $10^{-5}$ and each dilution was inoculated into 7-day-old embryos. Stunting and embryo deaths were recorded up to $10^{-4}$ dilution (Table 2). As expected, the most severe effects on the embryos, in terms of number of early deaths and dwarfing, were seen with the highest concentration of virus (i.e. at neat and $10^{-1}$ dilutions). There were few deaths at $10^{-2}$ and $10^{-3}$ dilutions, and none at $10^{-4}$ dilution. Changes such as dwarfing and liver necrosis in embryos still alive at day 11 post inoculation indicated that infectious virus was still present at these dilutions. An estimated infectivity titre of $10^4$ embryo infectious doses provides an explanation for the failure so far, to see virus particles by EM, since a virus particle titre of $>10^5$ or even $>10^6$ is often stated as being required in order to see particles in EM.

TABLE 2

Pattern of embryo deaths following inoculation of different infectious doses of 11672 virus.

| Inoculum dilution | Days post inoculation | | | | | | Findings with embryos alive at day 11 |
|---|---|---|---|---|---|---|---|
| | 3 | 4 | 5 | 6 | 7 | 10 | 11 | |
| Undiluted | | | 1 | 2 | 1 | 3 | | 1 small |
| −1 | 1 | | 1 | | 1 | 5 | | |
| −2 | | | | | 1 | 1 | | All 6 very small 4 liver necrosis |
| −3 | | | | | 1 | 1 | | All 6 small 2 liver necrosis |
| −4 | | | | | | | | 4 normal 4 small, liver necrosis |
| −5 | | | | | | | | All normal |

8 eggs were inoculated for each dilution.

All dead eggs at day 7 were stunted, haemorrhagic and with liver necrosis

Remaining embryos at day 11 were killed and examined

The effect of embryo infection with 11672 virus on hatchability was investigated in a further experiment. The 11672 virus embryo homogenate (2p EH) was inoculated into 7-day-old embryos, at 3 dilutions ($10^{-3}$, $10^{-4}$, $10^{-5}$), with 30 embryos for each dilution. 24 embryos were left uninoculated as controls. All embryos which died from day 8 post inoculation were checked. All were very small compared to controls, with evidence of hemorrhaging and necrosis of the liver. In addition 8 eggs from each dilution were opened at day 12 post inoculation and the embryos examined, with results as follows:

$10^{-3}$ dilution: 4/8 embryos were small compared to controls, 3/8 were very stunted, with obvious necrosis of the liver, 1/8 was normal.

$10^{-4}$ dilution: 3/8 very stunted, 2 of these with liver necrosis; 5/8 normal.

$10^{-5}$ dilution: 8/8 normal

The eggs surviving on day 13 post inoculation were transferred to an incubator and allowed to hatch.

TABLE 3

Effect of 11672 virus titre on hatchability

| Inoculum dilution | Number of eggs incubated at 13 days post inoculation | Deaths before day 13 | Number hatched | Dead in shell | % Hatched |
|---|---|---|---|---|---|
| Control (uninoculated) | 15 | 1 | 11 | 4 | 73% |
| $10^{-3}$ | 11 | 11 | 3 | 8 | 27% |
| $10^{-4}$ | 15 | 7 | 5 | 10 | 33% |
| $10^{-5}$ | 17 | 5 | 5 | 12 | 29% |

All chicks, which hatched, were very weak, and took a long time to get out of the egg.

All embryo inoculations so far had used the yolk sac route of inoculation, and embryo deaths and stunting had been a consistent finding. The chorioallantoic membrane (CAM) route of inoculation has been successful in some viral studies, since, if the agent grows in the CAM or can be adapted to grow in the CAM, a higher concentration of virus may result, making identification easier. Also, in the past cryostat sections from infected CAM, have been used for serology studies using indirect immunofluorescence. In addition CAMs from infected eggs are normally harvested at 4 days post inoculation, which shortens the isolation procedure (up to 12 days following yolk sac inoculation). The 11672 virus (1p EH) was therefore inoculated onto the CAMs of 9-day-old embryos, and harvested 4 days later. White foci and some thickening of the CAM was observed, indicating virus growth. Thickened areas of CAM were frozen and cryostat sections cut for immunofluorescent staining. The affected areas were excised, homogenised and re-inoculated onto the CAMs of 9-day-old embryos. Again, thickening of the inoculated CAMs was evident. The material has now been passaged 4 times by CAM inoculation. No virus was observed when CAM preparations were examined by EM, suggesting that virus yields were low.
Antigenic Characterisation of Infectious Agent 0.1 ml of the 11672 virus whole embryo homogenate was inoculated orally and intramuscularly into 12×1-day-old SPF chicks in an isolator. The birds were boosted with a second oral inoculation at 6 weeks of age, then bled and sacrificed 2 weeks later. No obvious clinical signs were seen in the inoculated birds throughout this period. The serum from the birds was collected, pooled and stored at −20° C. (Antiserum 1). A second group of 1-day-birds was inoculated intramuscularly and bled out after 5 weeks. The serum was collected, pooled and stored at −20° C., as before (Antiserum 2).

The 11672 virus embryo homogenate (2p EH) was inoculated onto SPF chick embryo liver cell cultures in 25 cm² plastic flasks. No virus like cytopathic effect (CPE) was observed after 7 days incubation at which time the cells were scraped from the flask, resuspended and re-inoculated onto fresh cultures (second pass). No CPE was observed after the second pass, or after a third pass in CEL cultures as above.

The 11672 virus embryo homogenate (2p EH) was inoculated undiluted and at ¹⁄₁₀ dilution, onto SPF chick embryo liver (CEL) cell cultures growing on 13 mm circular coverslips, and incubated at 30° C. for 48 hours. The coverslips were then fixed in acetone for 10 minutes, air dried and stained with Antiserum 1 (above) for 1 hour at 37° C. After washing in several changes of PBS, the coverslips were stained again with an FITC anti-chicken conjugate for 1 hour, washed, mounted in buffered glycerol and examined under U.V. illumination. At both dilutions of the inoculum, positive immunofluorescence was observed in single cells. The immunofluorescence was cytoplasmic, and often granular in nature. This result showed that embryo-passaged virus was capable of undergoing partial replication in CEL cells, but that replication did not result in CPE.

Indirect immunofluorescence (IIF), performed with Antiserum 1, was also successful in detecting virus antigen in cryostat sections of embryonic kidneys and CAM from 11672 virus-infected eggs. This confirmed that the thickening/pocks detected in CAMs were associated with the virus and also identified a possible site (i.e. kidney) of replication of the virus in the experimentally-inoculated chick embryos.

Exploratory testing by IIF showed that Antiserum 1 stained CEL coverslip cultures that were infected with FP3 virus, an enterovirus-like virus (ELV) that was isolated from dead-in-shell chicks in the 1980s. In addition antiserum raised to FP3 in previous research (McNulty et al., 1990) was shown to react by IIF with CEL coverslip cultures infected with 11672 virus. Cross-neutralisation tests have not yet been performed.

On the basis of the IIF results, it was concluded that 11672 virus is an enterovirus-like virus (ELV), that is antigenically related to FP3 virus. Although the IIF test will detect viruses that share a common group antigen, it cannot distinguish viruses from different serotypes.

Nucleotide Sequence Characterisation of 11672 Virus as Novel Chicken Astrovirus

Nucleotide sequence studies of isolate 11672

The following primer sequences were obtained to allow the amplification of Astrovirus RNA polymerase gene sequence by RT-PCR

```
AstPoI-1F
5'-GAYTGGACNMGNTAYGAYGGNACNATNCC    SEQ ID NO 8

AstPoI-1R
5'-YTTNACCCACATNCCRAA                SEQ ID NO 9
```

Wherein Y=C or T; M=A or C; R=A or G and N=deoxyinosine (I)

One-step RT-PCR was carried out using Ready-To-GO RT-PCR beads from Amersham Pharmacia.

| Temp   | Time   | Cycles |
|--------|--------|--------|
| 42° C. | 30 min | 1      |
| 94° C. | 5 min  | 1      |
| 94° C. | 60 sec | 45     |
| 45° C. | 60 sec |        |
| 72° C. | 90 sec |        |
| 72° C. | 5 min  | 1      |

| F-primer  | R-prime   | Size    |
|-----------|-----------|---------|
| AstPol-1F | AstPol-1R | ~411 bp |

Seq ID No. 1 and Seq ID No. 2 are the nucleotide (nt) sequences that are specific to the chicken astrovirus type 3 (CAstV-3) (isolate 11672). This is the 391 nt that are flanked by the degenerate primers designed to amplify astrovirus sequences in the RNA polymerase gene region. The sequences of 2 clones are shown. These differ at 4 nt positions (99.0% nt identity)

The nt sequence of the corresponding region of 1 clone of isolate FP3 is also shown as Seq ID No. 3. This differs from clone 1 of 11672 virus at 20 nt positions (94.9% nt identity).

Blast searches indicate that the 391 nt region shares 65% nt identity with Turkey Astrovirus type 1 (GenBank Accession number: Y15936), 61% nt identity with avian nephritis virus (GenBank Accession number: AB033998) and 60% nt identity with human astrovirus type 1 (GenBank Accession number: Z25771).

11672 and FP3 sequences ID Nos 1, 2 and 3 referred to above.

```
Seq ID No. 1
11672 Clone 1
AAAGCCCTTGTTTTGGCGCATTAGGCAGATTCGGTTTTTTTTTTAGC

CTCAAAGTATAAGACGCAGGAAAACAAGGAGCTGTTTGATTGGTACA

CCAAAAACCTTTTGGAGAAGGTGATATTGTTACCTACTGGGGAAGTGT

GCCAAATAAAGCGAGGAAATCCTTCAGGGCAATTTTCTACCACCGTG

GATAACAACATGTGCAACGTATGGTTAACCACCTTTGAAATAGCATGG

CTCCACCGCAAACAACGGGGCAGACTACCAACCCCAGCTGAATTGC

GTGAAAACGTTTGTTATATTTGCTACGGTGATGACAGGCTCTTATCAG
```

-continued

TTTCGAGAGACTTTGTCATTTATGAGCCTGAAACTGTGGTAGCAATGT

ACGCAGATGTA

Seq ID No. 2
11672 Clone 2
AAAACCCTTGTTTTGGCGCATTAGGCAGATTCGGTTTTTCTTTTTAGC

CTCAAAGTATAAGACGCAGGAAAACAAGGAGCTGTTTGATTGGTACA

CCAAAAACCTTTTGGAGAAGGTGATATTGTTACCTACTGGGGAAGTGT

GCCAAATAAAGCGAGGAAATCCTTCAGGGCAACTTTCTACCACCGTG

GATAACAACATGTGCAACGTATGGTTAACCACCTTTGAAATAGCATGG

CTCCACCGCAAACAACGGGGCAGACTACCAACCCCAGCTGAATTGC

GTGAAAACGTTTGTTATATTTGCTACGGTGATGACAGGCCCTTATCAG

TTTCGAGAGACTTTGTCATTTATGAGCCTGAAACTGTGGTAGCAATGT

ACGCAGATGTA

Seq ID No. 3
FP3 Clone 1
AAAGCCCTTGTTTTGGCGTATTAGGCAGATTCGGTTTTTCTTCTTAGC

CTCAAAGTATAAGACGCAGGAAAACAAGGACCTCTTTGATTGGTACA

CCAAAAACCTCTTGGAGAAGGTGATATTGTTACCTACTGGAGAAGTGT

GCCAAATAAAGCGAGGGAATCCTTCAGGGCAATTTTCTACTACCGTG

GATAACAACATGTGCAATGTATGGCTAACCACCTTTGAAATAGCATGG

CTTCACCGCAAACAACGGGGTAGATTACCAACCCCAGCTGAATTGCG

TGAAAATGTTTGTTATATTTGCTACGGTGATGATAGGCTCTTATCAGTT

TCAAGAGACTTTGTCATTTATGAGCCTGACACTGTGGTAGCGATGTAC

GCTGATGTA

This sequence data shows that 11672 virus and FP3 virus are very closely related at the nucleotide sequence level and that both are likely to be isolates of the same virus species. This sequence data is consistent with the finding that 11672 virus and FP3 are antigenically similar, as demonstrated by indirect immunofluorescence. On the basis of the levels of nucleotide identity shared with other astrovirus species, the virus species, of which 11672 and FP3 are isolates, is considered to be a novel chicken astrovirus, which the inventors have named chicken astrovirus type 3 (CAstV-3)

Nucleotide sequence corresponding to the 3.2 kb fragment at the 3' end of the virus genome was produced by RT-PCR using an oligo dT based forward primer that binds to the Poly A tract at the 3' end of the astrovirus genome and a reverse primer selected from within the sequence of 391 nucleotide fragment amplified by the degenerate primer strategy (SEQ ID No 1-3). The 3.2 kb fragment was cloned using the pTOPO vector and sequenced using a primer-walking strategy beginning with the forward and reverse M13 primers that are specific to the plasmid vector. Combining the nucleotide sequence specific to the 391 nucleotide fragment of 11672 virus with that determined for the 3.2 kb fragment gives a total sequence of 3265 nucleotides. This sequence encompasses 730 nucleotides at the 5' terminus of the astrovirus ORF 1b, which encodes the astrovirus RNA dependent RNA polymerase, a small intergenic sequence of 24 nucleotides, the complete astrovirus ORF 2 (2217 nucleotides), which encodes the capsid protein region, and the 3' untranslated region (UTR) of 276 nucleotides (excluding the Poly A tail).

The nucleotide sequence of the 3265 nucleotide fragment is as follows:—

SEQ ID No 4
AAAGCCCTTGTTTTGGCGCATTAGGCAGATTCGGTTTTTTTTTTAGC

CTCAAAGTATAAGACGCAGGAAAACAAGGAGCTGTTTGATTGGTACA

CCAAAAACCTTTTGGAGAAGGTGATATTGTTACCTACTGGGGAAGTGT

GCCAAATAAAGCGAGGAAATCCTTCAGGGCAATTTTCTACCACCGTG

GATAACAACATGTGCAACGTATGGTTAACCACCTTTGAAATAGCATGG

CTCCACCGCAAACAACGGGGCAGACTACCAACCCCAGCTGAATTGC

GTGAAAACGTTTGTTATATTTGCTACGGTGATGACAGGCTCTTATCAG

TTTCGAGAGACTTTGTCTTTTATGAGCCTGAAACTGTGGTAGCAATGT

ACGCAGATGTATTCGGCATGTGGGTGAAGCCAGAGAATGTGAAGGTA

AGAAATACACTTAGTGGTCTCTCTTTCTGTGGTATGACAATTACAAAA

AATCAGCATGGCCGTTATGTTGGTATTCCTAATGTCAATAAAATACTG

TCCACTCTACGGTCTCCTACAAAGCGCCTTCCAAATGTAGAAGCACTA

TGGGGTAAGTTGATATCATTAAGAATTCTGTGTGAGAATGCAGATCCC

GACGTAAAGGATTACTTAGATAGGCAGATCAATTGCGTCGAGGAGTA

TGCCGCTGCTGAAGAAATACAGTTACCAGAAGTCGGGCCCGACTTCT

TTCAGAAAATCTGGTAGAGGGATGGACCGAAATATAGCAGCATGGCC

GATAAGGCTAGCGCGCAGAAGGAGAAAACAACAAGGCGCGGACGTG

GCCGTTCTCGATCTAGGTCACGTTCTCGTTCCCGTTCTAGGAATCGT

GTCAAGAAAACTGTCACGATAGTTGAATCTAAGAAAACCCCATCTAGA

TCTATATTAAGAAAAGAACTTGAAATCATGAGAGAAGGGATAGGAGG

CGTTTTAGGAAGATTGAAAAAAAATTAAATGGCCCTAAAATACATGAT

CGCATGGCAGTCACAACTACACTTGGAGTCCTCACTGGAAATTCTGA

CAATAATTTGGAAAGGAAAATGAGAGCTCTTCTTAACCCATTGCTTTT

GAAATCTCAAAACACTGGGGCCTCAGCATCCCCACTTTCCCTTAGGG

CATCTCAGTATTCAATGTGGAAGATACAGAAATGTGTTGTAAAATTTG

TTCCCCTAGTTGGGGCTGCTAATGTGGCAGGTAGTGTATCCTTTGTG

TCTCTGGATCAGGATGCAACCTCCTCCCAGCCTGAATCACCTGATAC

GATAAAGGCAAAGGTGCATGCAGAAGTTGCAATTGGACAAAGATTTA

ATTGGAACGTTCAATCTAGATACCTGGTCGGACCCCGTTCTGGTTGG

TGGGGCATGGATACTGGTGAGTCACCAACTGATACAGTTGGACCAGC

CCTTGACTTTTGGAATCTTTATAGAACAGTGAACACACTTCAAACTGG

CTCAACATCGCAGGCATACACTGGACCATTGTTTTCTATTGAAGTGTA

TACGGTGTATGTTTTTCAGGTTACGAACCAAAGCCTGCGCTGGCGA

CCATGACAAATTCAACTTTTGAGAGTCAGCAGGGGGTGACCATAACA

AATGGTGCTAATGGTGAACTTCTGCTCAATGTTCCACGGCGATCGAG

TCTTGCCGAAGGGCTGCGTGAAAAGGAAGTATTATACCGCGGCCAAA

ACCAAACGGGTGGTGTCGGTGAGGTACTGTGGGCGGTGGCATCAGG

AGCTGTTGAAGGAGCTGCAGAAGCGTTGGGCCCATGGGGATGGTTA

-continued
```
CTGAGAGGTGGCTGGTGGGTGATAAAGAAGTTGTTTGGACGGAGCG

CTGAAAATGAAAGTGACGATTATGTGATGTACTCGTCTATTGAGGATG

CCAACAAAGATAGTAGGATCTATCAAACGGTATCCAGTGCGGTCCCT

GTTCAACAAGGTCCTCTGGTTCTCACCCAAATCTCATCCCCAAATGTT

AATCAAGCTGGGGGTGTTGTGCAGGTAGGTACAACAATTGCCACTGA

TTACTTGCCACTATCTCAGGCCCAGGTTCCGCTTTTAGAGAACATTCT

TTACTCCAGCACTGGGCAGCCTGTGACATCAACTAAGAGCCATACTA

TGAGGATCACTGGGTTTCCAGCCTCGAAATTGGTAACATCAACGTCG
```

-continued
```
TCGCAATGGTTGGGGACTACTGATACGAGTGTCCAAGCAACAAAGTG

GCTAATGTCGGATTATACAGACACTGGAGTGATATTTGGCTTTCCATA

CTCTGATGATTCCCCCGGGGAAACTTTTGGTAACATTGGAGTAATACA

CACAGCCAAGTCGCTCATAAAAACGGTCACATCAAGGCGACAACGCG

GGCTACGCATGTCTCCACTTGTTTCGACATTGTTACCATCAACTTCTA

AGGGACCAACCCAGATGCTTAGTTGCTTTGACACGCCTTACTATTGG

ATTAGGGTTTGTGACAATACCTGCTCAAACAAACCCACAAATGGCGC

CGTGACACAGCGCTGCAATGCTTGGGGCGTTATGGTGGTGAGCTTA

GCACACAATAAAGTCTACATCTTGGCTGGTTATCCCGATTCTCAAACT

AGGGTACCACAACAACAACTAGTCTGGGACACTTTTGACTGGGATGC

TACATTTTCTACTGGCAGGATTTATAATACAACATGGCCAGGACTTTA

TGAAGAAAGTGATGATGAAACAGATGCCGAATCTGACATCTCCAGTC

TTTTTGACCCCGTTAATGAGGTTGAGCAGGACTTTCACTTCAAATGTA

GTCTGAAGACATCTGACTACTTGAAGGAGGAGGCTGATTATTGGAAA

GCAAAAGCACAACAATTGCTTATGGAGAAAGCAATGGGAAAAAATAAT

GACTCTCCTCCACTTGTCCGCTTTGAGAAGGGCGGACCTGAGCAGCA

AAAACAGCCTGCTAGCAGCCGCGGCCACGCCGAGTAGGATCGAGGG

TACAGCTGCACCTTCTTCATGGAGTTTTTATGCCATAATCAGGCTTTT

CTCCATGTAAATCAAGGCACCGGGGCCACGCCGAGCAGGAACGAGG

GTACAGTGCCGGGTTGACCCCACCTGAAAGGGGCGTCCGCCGGTGT

GATAATCACGACACCGGGGCCTGGTTTAAATCACAGATAATCACTCT

GTGTGTCAATCAGGTCTTTCGGGCGGTTTTGGAAACACTAGTTTTTAA

AACCAATTTGATTTTGAATTAGATTAATTGGCAAAAAAAAAAAAAAAA

A.
```

The capsid protein gene is 2217 nucleotides in length and encodes a protein region of 738 amino acids.

The amino acid sequence of the 738 amino acid capsid protein region is as follows:

```
SEQ ID No 5
madkasaqkekttrrgrgrsrsrsrsrsrnrvkktvtiveskktpsrsilrkelenherrdrrrfrkiekkln gpkihdrmavttttlgvltgnsdnnlerkmrallnplllksqntgasasplslraaqysmwkiqkcvvkfvpl vgaanvagsvsfvsldqdatssqpespdtikakvhaevaigqrfnwnvqsrylvgprsgwwgmdtg esptdtvgpaldfwnlyrtvntlqtgstsqaytaplfsievytvyvfsgyepkpalatmtnstfesqqgvtit ngangellllnvprrsslaeglrekevlyrgqnqtggvgevlwavasgavegaaealgpwgwllrggw wvikklfgrsaenesddyvmyssiedankdsriyqtvssavpvqqgplvltqisspnvnqaggvvqv gttiatdylplsqaqvpllenilysstgqpvtstkshtmritgfpasklvtstssqwlgttdtsvqatkwlmsd ytdtgvifgfpysddspgetfgnigvihtaksliktvtsrrqrglrmsplvstllpstskgptqmlscfdtpyy wirvcdntcsnkptngavtqrcnawgvmvvslahnkvyilagypdsqtrvpqqqlvwdtfdwdatfst griynttwpglyeesddetdaesdisslfdpvneveqdfhfkcslktsdylkeeadywkakaqqllme kamgknndspplvrfekggpeqqkqpassrghae
```

Knowledge of the nucleotide and predicted amino acid sequence of the capsid protein region can be exploited for a number of purposes including:

1) Use as a DNA vaccine, if the gene is cloned into a suitable expression vector. Such expression vectors may be also used to prime/immunise mice for the generation of antibody reagents.
2) Use to produce recombinant protein products by prokaryotic (eg *E. coli*) and eukaryotic (eg recombinant baculovirus infected insect cells, yeast) expression systems. Such proteins may be of use as subunit vaccines or to immunise mice for the generation of antibody reagents.
3) Use to generate capsid protein-specific peptides for immunisation or vaccine purposes.
4) Use of specific nucleotide sequences for the development of astrovirus 3-specific RT-PCR tests.

Serological Diagnosis of Chicken Astrovirus Type 3 in Breeder Flocks

Serum samples from breeder flocks aged approximately 22 weeks (just before lay) were tested for the presence of antibody to 11672 virus, an isolate of CAstV-3, by an indirect immunofluorescence assay using CEL coverslip cultures that had been infected with 11672 Virus. Sera were screened at 1:500 dilution in PBS and chicken antibodies were detected using an FITC-anti chicken Ig conjugate. Antibody was detected in 62/211 (29.4%) birds and in samples from 13/17 (76.5%) flocks. The relatively low-levels of seroconversion in some flocks suggested that some flocks were experiencing on-going infections at the point of lay (22 weeks) and that further infections of breeder birds were likely to occur when the breeders were in lay.

TABLE 4

Serology results for breeder flocks tested at 22 week-old. CEL coverslips infected with 11672 virus were used in an indirect immunofluorescence test to detect virus-specific antibody in chicken sera.

| No | Flock | House | Age | Res |
|----|-------|-------|-----|-------|
| 1  | A     | 1     | 22  | 11/20 |
| 2  | A     | 2     | 22  | 6/10  |
| 3  | B     | 1     | 22  | 7/30  |
| 4  | C     |       | 22  | 3/10  |
| 5  | D     | 1     | 22  | 9/10  |
| 6  | E     | 1     | 22  | 0/10  |
| 7  | F     | 1     | 22  | 0/10  |
| 8  | G     | 1     | 22  | 1/10  |
| 9  | H     | 1     | 22  | 4/10  |
| 10 | I     | 1     | 22  | 2/10  |
| 11 | J     | 1     | 22  | 4/9   |
| 12 | K     | 1     | 22  | 0/22  |
| 13 | L     | 1     | 22  | 4/10  |
| 14 | M     | 1     | 22  | 3/10  |
| 15 | N     | 1     | 22  | 2/10  |
| 16 | O     | 1     | 22  | 0/10  |
| 17 | O     | 2     | 22  | 6/10  |

Detection of Chicken Astrovirus Type 3 in Flocks Exhibiting Uneven Growth

Gut contents from sick chickens from flocks showing "uneven growth" were investigated for the presence of virus. This involved preparing 5-10% homogenates in MEM cell culture medium, clarification at 3000 rpm for 30 min, centrifugation of the clarified extract at 10,000 rpm for 30 min, and ultracentrifugation of the supernate through a cushion of 30% (w/w) sucrose in PBS. Samples of the 10,000 rpm supernate and resuspended sucrose pellet were inoculated into CEL cells grown on glass coverslips. After washing, the coverslip cultures were incubated for 48 hr, and then fixed by treatment with acetone. Fixed coverslips were incubated with antisera against 3 immunologically different ELVs including CAstV-3. The presence of infectious CAstV-3 was detected in samples from 1 broiler flock exhibiting uneven growth at days 5, 7 and 9 post hatching. The presence of 2 other immunologically different ELVs, namely avian nephritis virus (CAstV-1) and an ELV, exemplified by isolate "612", was also demonstrated. Negative contrast electron microscopy performed with crude and partially purified preparations of gut contents showed that such samples contained high levels of ELVs and rotaviruses.

An inoculum prepared from the gut contents of a sick chicken sourced from a flock exhibiting uneven growth was used to orally infect 1-day-old SPF chickens. These birds displayed feathering abnormalities at about 2-3 weeks and a 30% weight depression at 5 weeks of age. Electron microscopic examination of gut content samples obtained from birds killed at day 4, 6, 8, 10 and 15 revealed the presence of ELVs at all timepoints. Antiserum recovered from birds at 5 week-old were shown by indirect IF to contain antibodies to CAstV-3 and to a second different ELV. This experiment showed that the gut contents of the sick chicken used for inoculation contained CAstV-3 and suggested that this ELV may have been contributing to the growth depression.

Vaccination

A vaccine to CAstV-3 is likely to protect against sickness and growth depression in young chickens, and also to protect against vertical transmission from infected breeders and possible ill-effects on the developing embryo and hatched chick that vertically transmitted virus may cause.

Vaccine for administration to breeder birds, would have health benefits for the developing embryo and young growing chick. Vaccine may also be administered to the growing broiler chicks.

Detection of Virus

The presence of virus in samples may be detected by the growth of infectious virus in embryos or cell culture. Alternatively virus (or more correctly virus antigen) can be detected inside tissue samples from infected chickens using immunohistochemistry. This involves collecting fresh tissue, fixation of tissue in formalin, paraffin embedding, the cutting of very thin tissue sections and the use of virus-specific antibodies (eg monoclonal or highly specific polyclonal antiserum) to stain virus antigen in the tissue section. The bound antibodies would be detected by a secondary enzyme-antibody conjugate.

Virus antigen can also be detected in frozen tissue sections using antibodies in a similar way.

In the case of astrovirus, which infects the intestinal tract, virus is excreted sometimes in large amounts in feces.

The presence of virus antigen may be detected in feces samples or swabs using an antigen-detecting ELISA. Typically, this involves the use of a virus specific antibody (immobilised onto a plastic surface) to bind to and "capture" virus particles present in diluted feces samples. Captured virus particles are then reacted with another virus-specific antiserum that has been conjugated to an enzyme, such as horse radish peroxidase. The presence of bound conjugate is demonstrated by adding the enzyme substrate and its conversion to coloured product.

Chickens will respond to infection by producing antibodies to the CAstV-3. Antibodies in the serum can be detected using a variety of tests such as indirect immunofluorescence assay, virus neutralisation or ELISA, which is particularly useful for large sample throughput. Typically an indirect ELISA would involve immobilising virus or virus antigen to the plastic microtitre plate, reaction with serum dilutions to allow antibodies to bind, reaction with enzyme conjugated secondary anti-chicken Ig antibody, followed by reaction with enzyme substrate. Alternatively a blocking ELISA can be used. This would involve demonstrating the presence of virus-specific chicken antibodies by their ability to "block" the reaction between immobilised virus antigen and a virus-specific antibody (usually a monoclonal antibody)

Monoclonal antibody production and characterisation may be carried out and monoclonal antibodies may be used in the development of diagnostic tests such as tests used to detect serum antibody to the infectious agent.

Alternatively a PCR test may be used. Details of such a test are provided below

Figure 3:
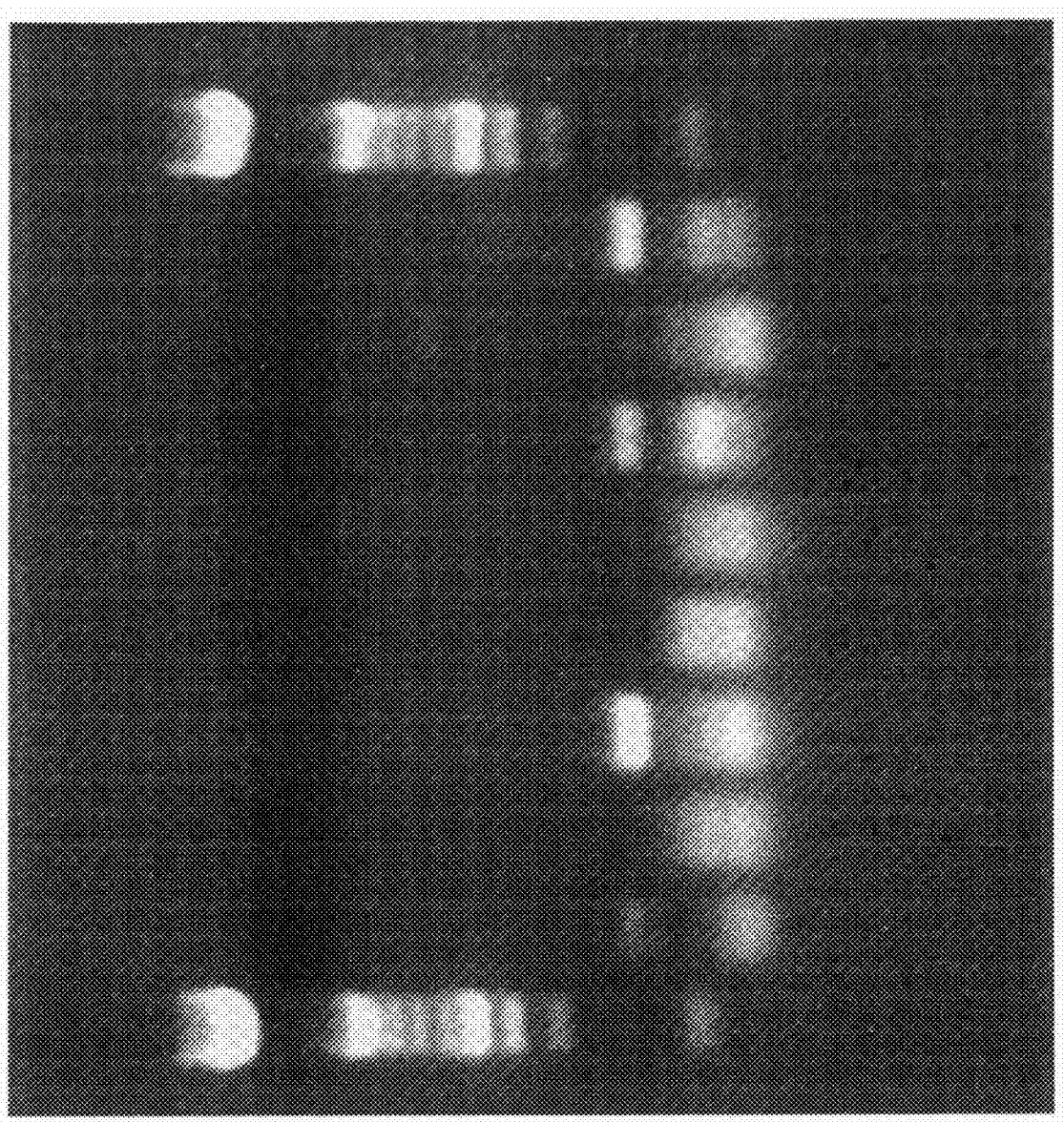
FIG. 3 shows agarose gel electrophoresis of RT-PCR results obtained with gut samples from day-old chicks, wherein the RT-PCR product is 187 bp.

A prototype RT-PCR test has been developed in which Forward (SEQ ID NO 6) and Reverse primers (SEQ ID NO 7) were based on conserved sequences found within the 391 nucleotide fragments specified by the 11672 and FP3 isolates (SEQ ID NO1-3) and amplified by the degenerate primer RT-PCR approach. The prototype test amplified a product of 187 base pairs (FIG. 3) and was found to be 10 to 100 fold more sensitive than the method involving inoculation of cell culture followed by indirect immunofluorescence. The prototype test successfully detected CAstV-3 in gut content samples obtained from 1-day-old chicks hatched from "sentinel" breeder chickens.

In this experiment, approximately 50 young females were sourced from a high health status flock. These were placed in pens within a diseased breeder flock, which was producing weak progeny chicks. Males from the diseased breeder flock were penned with the females. When the females began laying, eggs from the females were separately incubated, hatched and progeny chicks examined for the presence of CAstV-3. Twelve 1-day-old progeny chicks were investigated at weekly intervals. The chicks were killed and samples of intestine, liver, kidney and heart were collected from individual birds.

With each of the 12-chick submissions, the intestines from 6 chicks were pooled and processed by the ultracentrifugation method used to detect the 11672 ELV (above) in gut contents from uneven growth chicks. These preparations were inoculated onto CEL cells grown on coverslips, and, after 48 hr incubation, the inoculated cultures were stained for the presence of 11672 virus antigen using the previously described indirect IF test. No 11672 virus was detected in any of the preparations produced from the progeny submissions. (Table 5)

RNA was extracted from aliquots of the pooled intestinal samples (produced by ultracentrifugation) and tested by the prototype RT-PCR test. Of the 13 samples tested, 8 were positive for 11672 virus RNA. Positive samples were obtained intermittently from early submissions (Jul. 3, 2005) to some of the late submissions (May 31, 2005). These results indicated that the sentinel adults had become infected with 11672 virus present in the house and that vertical transmission was likely to have occurred. The detection profile, in which positive samples were detected over a 12-week period, suggested that spread of the 11672 virus was slow or that virus was transmission from the infected parent birds continued for long periods. Work is ongoing to determine whether the detection of CAstV-3 is associated with weakness or growth retardation problems in the progeny chicks.

TABLE 5

Detection of CAstV-3 in progeny chicks obtained from Sentinel breeder chickens

| Submission/Date | IIF with CEL cells | RT-PCR |
|---|---|---|
| 1: 21 Feb. 2005 | — | Nt |
| 2: 28 Feb. 2005 | — | Nt |
| 3: 7 Mar. 2005 | — | + |
| 4: 14 Mar. 2005 | — | + |
| 5: 21 Mar. 2005 | — | − |
| 6: 30 Mar. 2005 | — | + |
| 7: 4 Apr. 2005 | — | − |
| 8: 11 Apr. 2005 | — | − |
| 9: 18 Apr. 2005 | — | + |
| 10 25 Apr. 2005 | — | − |
| 11: 3 May 2005 | — | − |
| 12: 9 May 2005 | — | + |
| 13: 16 May 2005 | — | + |
| 14: 23 May 2005 | — | + |
| 15: 31 May 2005 | — | + |
| 16: 6 Jun. 2005 | — | Nt |

Nt: not tested

The invention now being fully described, it will be apparent to one of ordinary skill in the art that changes and modifications may be made thereto without departing from the scope of the claims.

The invention claimed is:

1. An isolated astrovirus strain designated, CAstV-3, wherein said strain is that deposited under Accession number CNCM I-3541 at CNCM, Institute Pasteur on 15 Dec. 2005.

2. An isolated polynucleotide having a nucleotide sequence which has at least 95% sequence identity to the nucleotide sequence as set forth in SEQ ID NO:4 and encodes an amino acid sequence that is capable of generating an immunogenic response against CAstV-3.

3. An isolated polynucleotide of claim 2 having the nucleotide sequence as set forth in SEQ ID NO:4.

4. A gene construct comprising an isolated polynucleotide having a nucleotide sequence as claimed in claim 2 and a control sequence.

5. A vector comprising an isolated polynucleotide as claimed in claim 2 and a promoter which is operably linked to said nucleotide sequence.

6. A method of producing a polypeptide encoded by a polynucleotide as claimed in claim 2, the method including the steps of:
   (i) contacting at least one of a bacterial cell, an insect cell via a baculovirus, a yeast cell, and a plant cell with a vector comprising a polynucleotide as claimed in claim 2 and a promoter which is operably linked to said nucleotide sequence, and
   (ii) cultivating at least one of said bacterial cell, said insect cell, said yeast cell, and said plant cell under conditions suitable for the production of polypeptide.

7. A composition comprising:
   (i) at least part of an isolated astrovirus strain designated CAstV-3, or
   (ii) at least one polynucleotide which has at least 95% sequence identify to the nucleotide sequence as set forth in SEQ ID NO:4 and encodes an amino acid sequence that is capable of generating an immunogenic response against CAstV-3.

8. A composition as claimed in claim 7 further comprising a pharmaceutical carrier or diluent.

9. A vaccine for immunisation against growth depression in an avian wherein said vaccine comprises a composition as claimed in claim 7 and an adjuvant.

10. A method of vaccinating an avian against CAstV-3 comprising the step of providing to said avian an immunologically effective amount of a vaccine for immunisation against growth depression in the avian wherein said vaccine comprises a composition, comprising:
   at least one polynucleotide having a nucleotide sequence which has at least 95% sequence identity to the nucleotide sequence as set forth in SEQ ID NO:4, and encodes an amino acid sequence that is capable of generating an immunogenic response against CAstV-3.

11. An isolated polynucleotide that encodes the polypeptide SEQ ID NO:5.

12. An isolated polynucleotide having at least 95% sequence identity to the segment of SEQ ID NO:4 consisting of nucleotides 755 to 2968.

13. An isolated polynucleotide according to claim 12 having a nucleotide sequence consisting of nucleotides 755 to 2968 of SEQ ID NO:4.

14. A composition comprising an isolated polynucleotide according to claim 11 and a pharmaceutical carrier or diluent.

15. A composition comprising an isolated polynucleotide according to claim 12 and a pharmaceutical carrier or diluent.

16. A composition comprising an isolated polynucleotide according to claim 13 and a pharmaceutical carrier or diluent.

17. A vaccine for immunisation against growth depression in an avian wherein said vaccine comprises a composition as claimed in claim 14 and an adjuvant.

18. A vaccine for immunisation against growth depression in an avian wherein said vaccine comprises a composition as claimed in claim 15 and an adjuvant.

19. A vaccine for immunisation against growth depression in an avian wherein said vaccine comprises a composition as claimed in claim 16 and an adjuvant.

20. A method of vaccinating an avian against growth depression comprising the step of providing to said avian an immunologically effective amount of a vaccine according to claim 17.

21. A method of vaccinating an avian against growth depression comprising the step of providing to said avian an immunologically effective amount of a vaccine according to claim 18.

22. A method of vaccinating an avian against growth depression comprising the step of providing to said avian an immunologically effective amount of a vaccine according to claim 19.

* * * * *